(12) United States Patent
Zhao

(10) Patent No.: US 12,100,495 B2
(45) Date of Patent: Sep. 24, 2024

(54) FOLLOW-UP FORM MANAGEMENT METHOD APPLIED TO HEALTH MANAGEMENT SYSTEM

(71) Applicant: BOE TECHNOLOGY GROUP CO., LTD., Beijing (CN)

(72) Inventor: Lei Zhao, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 17/919,593

(22) PCT Filed: Aug. 6, 2021

(86) PCT No.: PCT/CN2021/111252
§ 371 (c)(1),
(2) Date: Oct. 18, 2022

(87) PCT Pub. No.: WO2022/068396
PCT Pub. Date: Apr. 7, 2022

(65) Prior Publication Data
US 2023/0187040 A1    Jun. 15, 2023

(30) Foreign Application Priority Data

Sep. 30, 2020 (CN) .......................... 202011063268.1

(51) Int. Cl.
*G16H 15/00* (2018.01)
*G06F 40/174* (2020.01)
(Continued)

(52) U.S. Cl.
CPC .......... *G16H 15/00* (2018.01); *G06F 40/174* (2020.01); *G06F 40/186* (2020.01); *G06F 3/0482* (2013.01); *G16H 40/20* (2018.01)

(58) Field of Classification Search
CPC .... G06F 40/186; G06F 40/174; G06F 3/0482; G16H 15/00; G16H 40/20
See application file for complete search history.

(56) References Cited

U.S. PATENT DOCUMENTS 9,870,312 B2 * 1/2018 Cai ..................... G06F 11/3684
11,295,396 B1 * 4/2022 McDonald ........... G06V 30/412
(Continued)

FOREIGN PATENT DOCUMENTS

CN      101216763 A    7/2008
CN      102576376 A    7/2012
(Continued)

OTHER PUBLICATIONS

International Search Report and Written Opinion for International Application No. PCT/CN2020/131561 issued by the International Searching Authority on Mar. 3, 2021.
(Continued)

*Primary Examiner* — Kyle R Stork

(57) ABSTRACT

A follow-up form management method applied to a health management system includes: in response to an operation instruction for opening a scale making tool interface, displaying the scale making tool interface, the scale making tool interface including a field display area and an editing area; in response to an operation instruction for making a follow-up form, making the follow-up form in the editing area; in response to an operation instruction for opening a follow-up creating interface, displaying the follow-up creating interface, the follow-up creating interface including an options menu, and the options menu including options corresponding to the generated follow-up form; and in response to an operation instruction for creating a follow-up task, creating a follow-up task, the follow-up form included in the follow-up task being a follow-up form corresponding
(Continued)

to an option selected from the options menu under the operation instruction for creating the follow-up task.

17 Claims, 24 Drawing Sheets

(51) Int. Cl.
  *G06F 40/186* (2020.01)
  *G06F 3/0482* (2013.01)
  *G16H 40/20* (2018.01)

(56) References Cited

U.S. PATENT DOCUMENTS

| | | | |
|---|---|---|---|
| 11,562,331 B1* | 1/2023 | Hsu | G06Q 10/10 |
| 2007/0156032 A1* | 7/2007 | Gordon | G16H 50/20 |
| | | | 128/923 |
| 2013/0073306 A1 | 3/2013 | Shlain et al. | |
| 2014/0108048 A1* | 4/2014 | Cohn | G16H 10/60 |
| | | | 705/3 |
| 2014/0249855 A1 | 9/2014 | Moore | |
| 2014/0337051 A1 | 11/2014 | Karpf et al. | |
| 2017/0116373 A1 | 4/2017 | Ginsburg et al. | |
| 2017/0169175 A1 | 6/2017 | Graff et al. | |
| 2019/0272919 A1 | 9/2019 | Frandsen et al. | |

FOREIGN PATENT DOCUMENTS

| | | |
|---|---|---|
| CN | 106779613 A | 5/2017 |
| CN | 106934244 A | 7/2017 |
| CN | 107066812 A | 8/2017 |
| CN | 107436988 A | 12/2017 |
| CN | 107480418 A | 12/2017 |
| CN | 107506592 A | 12/2017 |
| CN | 108170654 A | 6/2018 |
| CN | 108447532 A | 8/2018 |
| CN | 108628905 A | 10/2018 |
| CN | 109461476 A | 3/2019 |
| CN | 109887559 A | 6/2019 |
| CN | 110717320 A | 1/2020 |
| CN | 111222843 A | 6/2020 |
| WO | 0237337 A2 | 5/2002 |
| WO | 2018125280 A1 | 7/2018 |

OTHER PUBLICATIONS

Partial Supplementary European Search Report for European Application No. 20892087.6 issued by the European Patent Office on Dec. 19, 2022.
Extended European Search Report issued by the EPO for Application No. 20892087.6, dated Apr. 14, 2023.
First Office Action for Chinese Patent Application No. 202011063268.1 issued by the Chinese Patent Office on Jun. 12, 2024.
First Office Action for Chinese Patent Application No. 202011331863.9 issued by the Chinese Patent Office on Jun. 3, 2024.
Kai Wu, Research and Implementation of Medical Follow-up system based on the cloud computing, Dissertation Submitted to Zhejiang University of Technology for the Degree of Master, Mar. 13, 2017, Zhejiang University of Technology, with English Abstract.

* cited by examiner

100

Hypertensive Patient Follow-up Service Record Form

Follow-up date: [Select date and time]  Follow-up manner: [Please select]

Symptoms

- ☐ Asymptomatic
- ☐ Headache and dizziness
- ☐ Nausea and vomiting
- ☐ Dim eyesight and tinnitus
- ☐ Difficulty breathing
- ☐ Palpitations and chest tightness
- ☐ Nosebleeds (epistaxis)
- ☐ Numbness in the limbs
- ☐ Lower extremity edema Others: [                    ]

Physical signs

| | Current value | Target value to be adjusted to at time of next follow-up |
|---|---|---|
| Height (m) | | |
| Weight (kg) | | ※ |
| Body Mass Index (BMI) (kg/m²) | | ※ |
| Heart rate (beats/min) | | |
| Others | Please fill in other positive signs | |

Lifestyle guidance

| | Current situation | Target value to be adjusted to at time of next follow-up |
|---|---|---|
| Number of cigarettes per day | | ※ |
| Drinking amout per day (tael) | | ※ |
| Exercise | [Please select] ___ min/time ※ | [Please select] ___ min/time |
| Salt intake (salty/bland) | ○ Mild  ○ Moderate  ○ Severe ※ | ○ Mild  ○ Moderate  ○ Severe |
| Psychological adjustment | ○ Good  ○ Average  ○ Poor | |
| Medical compliance | ○ Good  ○ Average  ○ Poor | |

| Auxiliary examination | |
|---|---|
| Medication compliance | ○ Regular  ○ Intermittent  ○ Non-compliant |
| Adverse reactions to drugs | ○ No  ○ Yes  Please enter adverse reactions |
| Classification of this follow-up | ○ Control satisfaction  ○ Control dissatisfaction  ○ Adverse reactions  ○ Complications<br>Remark: |

Medication

| | Drug name | Usage | Frequency | Dose | Operation |
|---|---|---|---|---|---|
| This prescription | Drug name 1 | | | | 🗑 |
| | Drug name 2 | | | | 🗑 |
| | Drug name 3 | | | | 🗑 ⊕ |
| Prescriptions of other institutions | | | | | |

Referral

| Reason | |
|---|---|
| Referral institution | Referral department |
| Date of next follow-up: [Please select] | Signature of follow-up doctor |

Hypertensive Patient Follow-up Service Record Form

Follow-up date: 2018-12-04 11:34:25    Follow-up manner: Outpatient

Symptoms

- ☐ Asymptomatic
- ☑ Headache and dizziness
- ☑ Nausea and vomiting
- ☐ Dim eyesight and tinnitus
- ☐ Difficulty breathing
- ☐ Palpitations and chest tightness
- ☐ Nosebleeds (epistaxis)
- ☐ Numbness in the limbs
- ☐ Lower extremity edema Others:

Physical signs

|  | Current value | | Target value to be adjusted to at time of next follow-up |
|---|---|---|---|
| Height (m) | 1.76 | | |
| Weight (kg) | 90 | ※ | 87 |
| Body Mass Index (BMI) (kg/m²) | 28.9 | ※ | 26.7 |
| Heart rate (beats/min) | 78 | | |
| Others | Please fill in other positive signs | | |

Lifestyle guidance

|  | Current situation | | Target value to be adjusted to at time of next follow-up |
|---|---|---|---|
| Number of cigarettes per day | 7 | ※ | 3 |
| Drinking amount per day (tael) | 3 | ※ | 1 |
| Exercise | 5 times/week - 6 times/week  min/time | ※ | 5 times/week - 6 times/week  min/time |
| Salt intake (salty/bland) | ○ Mild  ○ Moderate  ● Severe | ※ | ○ Mild  ● Moderate  ○ Severe |
| Psychological adjustment | ○ Good  ○ Average  ● Poor | | |
| Medical compliance | ○ Good  ○ Average  ● Poor | | |
| Auxiliary examination | | | |
| Medication compliance | ○ Regular  ○ Intermittent  ● Non-compliant | | |
| Adverse reactions to drugs | ○ No  ● Yes  Please enter adverse reactions | | |
| Classification of this follow-up | ○ Control satisfaction  ○ Control dissatisfaction  ● Adverse reactions  ○ Complications  Remark: | | |

Medication

| | Drug name | Usage | Frequency | Dose | Operation |
|---|---|---|---|---|---|
| This prescription | Drug name 1 | | QD | | |
| | Drug name 2 | | QD | | |
| | Drug name 3 | | BID | | |
| Prescriptions of other institutions | | | | | |

Referral

| Reason | |
|---|---|
| Referral institution | |
| Referral department | |
| Date of next follow-up | 2019-01-04 |
| Signature of follow-up doctor | XXX |

Type 2 Diabetic Patient Follow-up Service Record Form

Follow-up date: 2018-12-04 11:34:25    Follow-up manner: Outpatient

Symptoms

- ☐ Asymptomatic
- ☑ Excessive thirst
- ☑ Excessive eating
- ☐ Excessive urination
- ☐ Blurred vision
- ☐ Infection
- ☐ Numbness of hands and feet
- ☐ Lower extremity edema
- ☐ Significant weight loss Others:

Physical signs

| | Current value | Target value to be adjusted to at time of next follow-up |
|---|---|---|
| Height (m) | 160 / 105 | |
| Weight (kg) | 180 | 174 |
| Body Mass Index (BMI) (kg/m²) | 28.9 | 26.7 |
| Dorsalis pedis artery pulse | ○ Palpation normal  ○ Weakened  Both sides / Left side / Right side | ○ Disappeared  Both sides / Left side / Right side |
| Others | Please fill in other positive signs | |

Lifestyle guidance

| | Current situation | Target value to be adjusted to at time of next follow-up |
|---|---|---|
| Number of cigarettes per day | 7 | 3 |
| Drinking amount per day (tael) | 3 | 1 |
| Exercise | 5 times/week - 6 times/week   min/time | 5 times/week - 6 times/week   min/time |
| Staple food (g/day) | 1000 | 800 |
| Psychological adjustment | ○ Good  ○ Average  ⊙ Poor | |
| Medical compliance | ○ Good  ○ Average  ⊙ Poor | |
| Auxiliary examination | | |
| Medication compliance | ○ Regular   ○ Intermittent   ⊙ Non-compliant | |
| Adverse reactions to drugs | ○ No  ⊙ Yes   Please enter adverse reactions | |
| Classification of this follow-up | ○ Control satisfaction  ○ Control dissatisfaction  ⊙ Adverse reactions  ○ Complications  Remark: | |

Medication

| | Drug name | Usage | Frequency | Dose | Operation |
|---|---|---|---|---|---|
| This prescription | Drug name 1 | | QD | | |
| | Drug name 2 | | QD | | |
| | Drug name 3 | | BID | | |

Prescriptions of other institutions

Referral

| Reason | |
|---|---|
| Referral institution | Referral department |
| Date of next follow-up | 2019-01-04 |
| Signature of follow-up doctor | XXX |

| No. | Form name | Form type | Time of making the form | Operation |
|---|---|---|---|---|
| 123456789456789bvc | Hypertensive Patient Follow-up Service Record Form | 111 | 2020-05-20 17:32:53 | |
| 123452389456789ybn | Hypertensive Patient Follow-up Service Record Form 7 | 22 | 2020-05-27 14:23:53 | |
| 1234567892236789thn | Coronary Heart Disease Follow-up Scale | 1 | 2020-06-10 10:24:34 | |
| 123436789456789mjh | Stroke Follow-up Scale | 222 | 2020-06-10 17:32:53 | |
| 123467894562389bvc | Antenatal Follow-up Form | 222 | 2020-06-11 10:19:14 | |
| 123456787556789bvc | Diabetes Follow-up Form | 222 | 2020-06-18 14:00:47 | |
| 123459894567894bvc | Health Assessment Form | | 2020-06-23 16:47:06 | |
| 123456478256789bvc | Diabetes Follow-up Form | c | 2020-06-24 17:28:40 | |

.# FOLLOW-UP FORM MANAGEMENT METHOD APPLIED TO HEALTH MANAGEMENT SYSTEM

CROSS-REFERENCE TO RELATED APPLICATIONS

This application is a national phase entry under 35 USC 371 of International Patent Application No. PCT/CN2021/111252, filed on Aug. 6, 2021, which claims priority to Chinese Patent Application No. 202011063268.1, filed on Sep. 30, 2020, which are incorporated herein by reference in their entirety.

TECHNICAL FIELD

The present disclosure relates to the field of medical information technology, and in particular, to a follow-up form management method applied to a health management system, an electronic device, and a computer-readable storage medium.

BACKGROUND

Forms are mainly used to implement data collection functions on web pages. At present, forms are applied in various industries. For example, in the medical industry, when a patient sees a doctor in a medical institution, the doctor needs to fill in an electronic medical record, including an outpatient medical record and an inpatient medical record. In addition, some medical institutions will also conduct patient evaluations, follow-ups, satisfaction evaluations, questionnaire surveys, etc.; alternatively, in the catering industry, companies need to conduct employee satisfaction evaluations and questionnaire surveys, and customer satisfaction evaluations and questionnaire surveys—all of which can be done by making corresponding forms.

SUMMARY

In one aspect, a follow-up form management method applied to a health management system is provided. The method includes: in response to an operation instruction for opening a scale making tool interface, displaying the scale making tool interface; the scale making tool interface including a field display area and an editing area, the field display area including a plurality of fields, the editing area being used for making a follow-up form, a follow-up form to be made including a plurality of target elements, and each target element being generated by a field;

In response to an operation instruction for making a follow-up form, making the follow-up form in the editing area; in response to an operation instruction for opening a follow-up creation interface, displaying the follow-up creation interface, the follow-up creation interface including an options menu, and the options menu including a plurality of options corresponding to the generated follow-up form; and in response to an operation instruction for creating a follow-up task, creating the follow-up task including a follow-up form, the follow-up form included in the follow-up task being a follow-up form corresponding to an option selected from the options menu under the operation instruction for creating the follow-up task.

In response to the operation instruction for making the follow-up form, making the follow-up form in the editing area, includes: receiving a first operation entered on the scale making tool interface, the first operation being used for selecting a field from the plurality of fields; in response to the first operation, displaying the selected field in the editing area; and receiving and responding to the first operation repeatedly, until fields corresponding to the plurality of target elements required by the follow-up form to be made are all displayed in the editing area, so as to generate the follow-up form.

In some embodiments, the follow-up creation interface includes a standard template area, and the standard template area includes a template classification selection box; the template classification selection box has a chronic disease options menu, and the chronic disease options menu includes a plurality of chronic disease options; each chronic disease option corresponds to a follow-up template, and each follow-up template includes a plurality of follow-up forms and an interval time corresponding to each follow-up form.

In response to the operation instruction for creating the follow-up task, creating the follow-up task including the follow-up form, includes: receiving a second operation entered in the standard template area, the second operation being used for selecting the template classification selection box; in response to the second operation, displaying the chronic disease options menu including the plurality of chronic disease options in the standard template area; receiving a third operation entered in the standard template area, the third operation being used for selecting a single chronic disease option from the plurality of chronic disease options; in response to the third operation, creating a plurality of follow-up tasks in the standard template area, each follow-up task including the follow-up form and a corresponding return visit time, the follow-up form being the follow-up form in the follow-up template corresponding to the selected chronic disease option, and the return visit time being obtained according to a date of creating the follow-up task and the interval time corresponding to the follow-up form.

In some embodiments, the method further includes: in response to an operation instruction for opening a follow-up template interface, displaying the follow-up template interface; the follow-up template interface including a template classification bar, and the template classification bar including the plurality of chronic disease options; in response to an operation instruction for creating a follow-up template, creating the follow-up template corresponding to the selected chronic disease option.

In some embodiments, the follow-up template interface further includes a template content bar; the template content bar includes a new button, and the template content bar is used for displaying the created follow-up template. In response to the operation instruction for creating the follow-up template, creating the follow-up template, includes: receiving a fourth operation entered in the template classification bar; wherein the fourth operation is used for selecting a chronic disease option from the plurality of chronic disease options and for selecting the new button; in response to the fourth operation, displaying a follow-up template creation dialog box on the follow-up template interface; wherein the follow-up template creation dialog box includes a follow-up form edit box and an interval time edit box as well as a confirm button and a cancel button, the follow-up form edit box has at least one form option related to the selected chronic disease option, and each form option corresponding to a generated follow-up form;

receiving a fifth operation entered in the follow-up form edit box, the fifth operation being used for selecting a form option from the at least one form option; in response to the fifth operation, displaying a name of a follow-up form corresponding to the selected form option in the follow-up form edit box; receiving a sixth operation entered in the interval time edit box, the sixth operation being used for setting the interval time corresponding to the selected chronic disease option; in response to the sixth operation, displaying the set interval time in the interval time edit box; receiving a seventh operation entered in the follow-up template creation dialog box, the seventh operation being used for selecting the confirm button; and in response to the seventh operation, displaying the follow-up template in the template content bar.

In some embodiments, the follow-up creation interface includes a custom area; the custom area includes at least one custom item, and each custom item includes a return visit content selection box; the return visit content selection box has a form options menu the form options menu includes a plurality of form options, and each form option corresponds to a generated follow-up form. In response to the operation instruction for creating the follow-up task, creating the follow-up task including the follow-up form, includes: receiving an eighth operation entered in the custom area, the eighth operation being used for selecting a return visit content selection box of a custom item; in response to the eighth operation, displaying a form options menu, provided in the return visit content selection box of the selected custom item, including a plurality of form options in the custom area; receiving a ninth operation entered in the custom area, the ninth operation being used for selecting a form option from the plurality of form options displayed in the custom area; and in response to the ninth operation, creating the follow-up task in the custom area, the follow-up task including a follow-up form corresponding to the selected form option.

In some embodiments, the follow-up task further includes a return visit date. The selected custom item by the eighth operation includes a return visit date sub-item. The return visit date sub-item has a fixed return visit date; or the return visit date sub-item has a date options menu including a plurality of return visit dates that are selectable.

In some embodiments, the method further includes: before creating the follow-up task including the follow-up form, in response to an operation instruction for opening a patient management interface, displaying the patient management interface; the patient management interface including basic information of at least one patient and an operation index item, and the operation index item including a follow-up index creation item. In response to the operation instruction for opening the follow-up creation interface, displaying the follow-up creation interface, includes: receiving a tenth operation entered on the patient management interface, the tenth operation being used for selecting a follow-up index creation item of a target patient; and in response to the tenth operation, displaying the follow-up creation interface; the follow-up creation interface further including a basic information area, and basic information of the target patient being displayed in the basic information area.

In some embodiments, the plurality of fields include at least one basic field, and each basic field includes at least one property to be edited. The field selected by the first operation is a basic field, after displaying the selected field in the editing area, in response to the operation instruction for making the follow-up form, making the follow-up form in the editing area further includes: in response to the first operation, displaying a properties menu of the basic field in the editing area, the properties menu including at least one property edit box; receiving an eleventh operation entered in the at least one property edit box, the eleventh operation being used for editing a property of the basic field in each property edit box; and in response to the eleventh operation, displaying the edited property in each property edit box to generate the target element.

In some embodiments, the properties menu further includes a save as commonly used field button. The method further includes: receiving a twelfth operation entered in the properties menu, the twelfth operation being used for selecting the save as commonly used field button; and in response to the twelfth operation, displaying the generated target element in the field display area as a commonly used field.

In some embodiments, the plurality of fields include at least two basic fields, and the at least two basic fields include a first basic field and a second basic field; the first basic field is used for generating a first target element, the second basic field is used for generating a second target element, and a corresponding relationship exists between the first target element and the second target element; at least one property edit box of the first basic field includes a data source property edit box. In response to the eleventh operation, displaying the edited property in each property edit box, includes; in response to the eleventh operation, displaying a data source property representing the corresponding relationship in the data source property edit box of the first basic field.

The method further includes; in response to an operation instruction for opening a follow-up task execution interface, displaying the follow-up task execution interface; the follow-up task execution interface including a follow-up form included in a follow-up task created for a target patient, the follow-up form included in the follow-up task created for the target patient including the first target element and the second target element, and the first target element and the second target element each having an edit box; receiving a thirteenth operation entered in the edit box of the second target element, the thirteenth operation being used for entering target content in the edit box of the second target element; in response to the thirteenth operation, displaying the target content in the edit box of the second target element, and automatically displaying content obtained according to the corresponding relationship represented by the data source property in the edit box of the first target element.

In some embodiments, the plurality of fields include a third basic field; the third basic field is used for generating a third target element, and at least one property edit box of the third basic field includes a data source property edit box. In response to the eleventh operation, displaying the edited property in each property edit box, includes; in response to the eleventh operation, displaying a data source property linked with a background database in the data source property edit box of the third basic field.

The method further includes: in response to an operation instruction for executing a follow-up task, displaying the follow-up task execution interface; the follow-up task execution interface including a follow-up form included in a follow-up task created for a target patient, the follow-up form included in the follow-up task created for the target patient including the third target element, and the third target elements having an edit box; receiving a fourteenth operation entered in the edit box of the third target element, the fourteenth operation being used for selecting the edit box of the third target element; and in response to the fourteenth operation, automatically displaying content in the background database linked with the data source property of the third target element in the edit box of the third target element.

In some embodiments, the plurality of fields include at least one commonly used field, and a commonly used field includes at least one edited property. The field selected by the first operation is a commonly used field, after displaying the selected field in the editing area, in response to the operation instruction for making the follow-up form, making the follow-up form in the editing area further includes: in response to the first operation, using the commonly used field displayed in the editing area as the target element.

In some embodiments, the plurality of fields include a plurality of commonly used fields, and the plurality of commonly used fields include at least one common commonly used field and at least one private commonly used field. The common commonly used field is able to be used as a target element in at least two types of follow-up forms to be made, and the private commonly used field is able to be used as a target element in one type of follow-up form to be made.

In some embodiments, the scale making tool interface further includes a form area and a submission bar; the form area is used for displaying a name of the generated follow-up form, and the submission bar includes a generate form button. In response to the operation instruction for making the follow-up form, making the follow-up form in the editing area further includes: receiving a fifteenth operation entered in the submission bar, the fifteenth operation being used for selecting the generate form button, so as to submit and save the generated follow-up form; and in response to the fifteenth operation, displaying the name of the saved follow-up form in the form area.

In some embodiments, the submission bar further includes a preview button. In response to the operation instruction for making the follow-up form, making the follow-up form in the editing area further includes: before receiving the fifteenth operation, receiving a sixteenth operation entered in the submission bar, the sixteenth operation being used for selecting the preview button to preview the generated follow-up form; and in response to the sixteenth operation, displaying the generated follow-up form in the editing area.

In some embodiments, the sixteenth operation is further used for selecting a preview effect of the form, the preview effect including a paper effect and an effect displayed on a screen of a mobile terminal. In response to the sixteenth operation, displaying the generated follow-up form in the editing area, includes: in response to the sixteenth operation, displaying the generated follow-up form in the editing area with the paper effect or with the effect displayed on the screen of the mobile terminal.

In some embodiments, the form area includes a list sub-area and an operation sub-area; the list sub-area includes a name of at least one saved follow-up form, and a saved form includes a plurality of set elements; the operation sub-area includes at least one import reference option, and each saved form corresponds to an import reference option.

In response to the operation instruction for making the follow-up form, making the follow-up form in the editing area further includes: receiving a seventeenth operation entered in the operation sub-area, the seventeenth operation being used for selecting an import reference option of the at least one import reference option; in response to the seventeenth operation, displaying a saved follow-up form corresponding to the selected import reference option in the editing area; the saved follow-up form corresponding to the selected import reference option being used as a basic form; receiving an eighteenth operation entered in a form creation interface; the eighteenth operation being used for modifying at least one set element of the plurality of set elements in the basic form; the at least one set element being inconsistent with the plurality of target elements of the follow-up form to be made; in response to the eighteenth operation, setting the at least one set element that is modified to generate a target element; and receiving and responding to the eighteenth operation repeatedly, until the plurality of set elements of the basic form are consistent with the plurality of target elements of the follow-up form to be made, so as to generate a new follow-up form.

In yet another aspect, an electronic device is provided. The electronic device includes a processor and a memory. The memory has stored thereon computer program instructions suitable for execution by the processor. When the computer program instructions are run on the processor, the processor performs one or more steps of the follow-up form management method as described in any one of the above embodiments.

In yet another aspect, a non-transitory computer-readable storage medium is provided. The computer-readable storage medium has stored thereon computer program instructions that, when run on a processor, cause the processor to perform one or more steps of the follow-up form management method as described in any one of the above embodiments.

BRIEF DESCRIPTION OF THE DRAWINGS

In order to describe technical solutions in the present disclosure more clearly, the accompanying drawings to be used in the description of some embodiments of the present disclosure will be introduced briefly below. Obviously, the accompanying drawings to be described below are merely accompanying drawings of some embodiments of the present disclosure, and a person of ordinary skill in the art can obtain other drawings according to these drawings. In addition, the accompanying drawings in the following description may be regarded as schematic diagrams, but are not limitations on an actual size of a product, an actual process of a method and an actual timing of a signal involved in the embodiments of the present disclosure.

FIG. 1A is a schematic diagram of a form to be made in a follow-up form management method, according to some embodiments of the present disclosure;

FIG. 1B is another schematic diagram of a form to be made in a follow-up form management method, according to some embodiments of the present disclosure;

FIG. 1C is a schematic diagram of another form to be made in a follow-up form management method, according to some embodiments of the present disclosure;

FIG. 2D is yet another schematic diagram of a scale making tool interface in a follow-up form management method, according to some embodiments of the present disclosure;

FIG. 2E is yet another schematic diagram of a scale making tool interface in a follow-up form management method, according to some embodiments of the present disclosure;

FIG. 2F is yet another schematic diagram of a scale making tool interface in a follow-up form management method, according to some embodiments of the present disclosure;

FIG. 2G is yet another schematic diagram of a scale making tool interface in a follow-up form management method, according to some embodiments of the present disclosure;

FIG. 4A is a schematic diagram of a follow-up creation interface in a follow-up form management method, according to some embodiments of the present disclosure;

FIG. 4B is another schematic diagram of a follow-up creation interface in the follow-up form management method, according to some embodiments of the present disclosure;

FIG. 6 is a schematic diagram of a follow-up management interface in a follow-up form management method, according to some embodiments of the present disclosure;

FIG. 7 is a schematic diagram of a follow-up task execution interface in a follow-up form management method, according to some embodiments of the present disclosure;

FIG. 12 is a preview effect diagram of a form made in a follow-up form management method, according to some embodiments of the present disclosure;

DETAILED DESCRIPTION

Figure 2A:
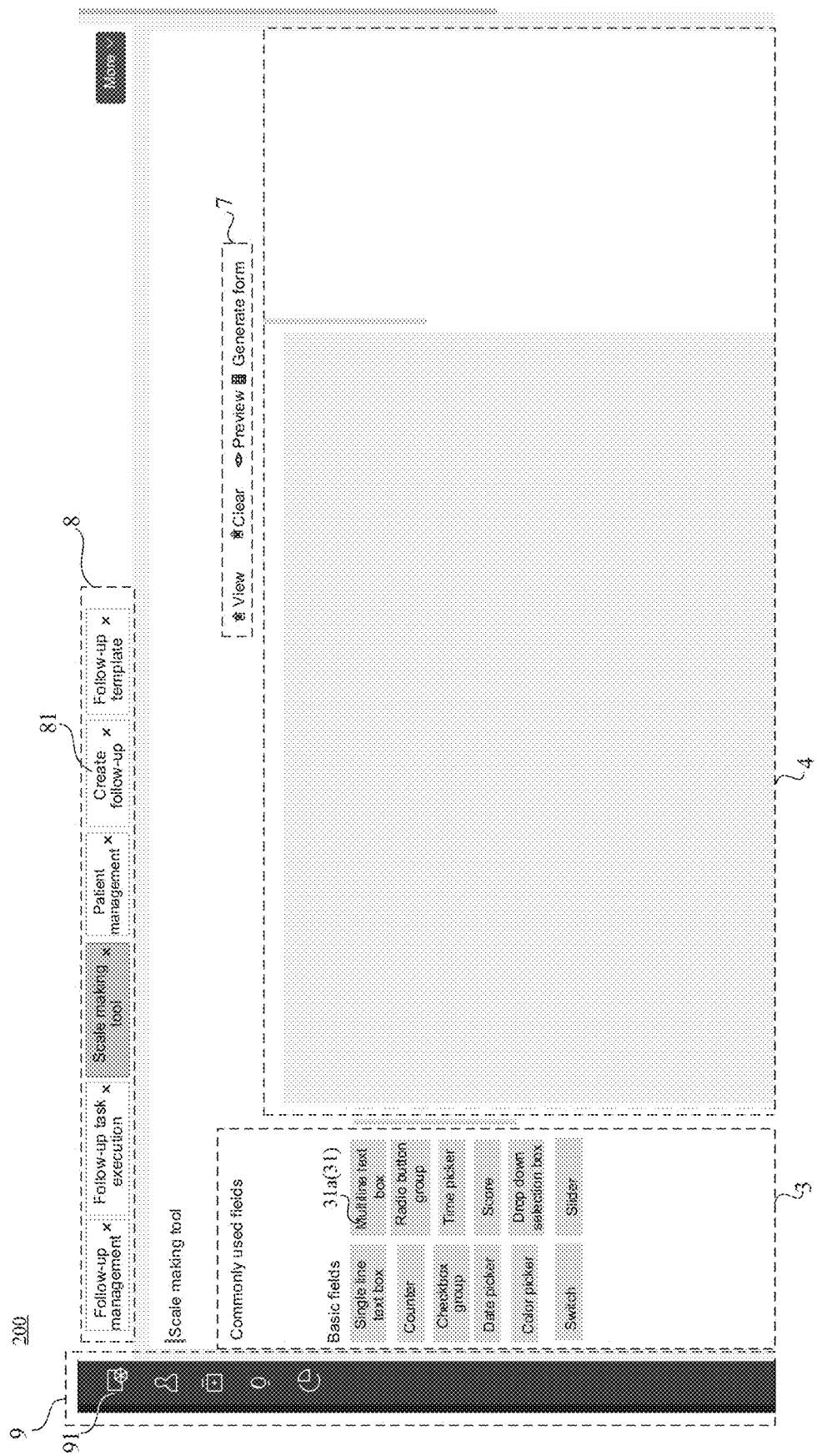
FIG. 2A is a schematic diagram of a scale making tool interface in a follow-up form management method, according to some embodiments of the present disclosure.

The technical solutions in some embodiments of the present disclosure will be described clearly and completely with reference to the accompanying drawings. Obviously, the described embodiments are merely some but not all of embodiments of the present disclosure. All other embodiments made on the basis of the embodiments of the present disclosure by a person of ordinary skill in the art shall be included in the protection scope of the present disclosure.

Unless the context requires otherwise, the term "comprise" and other forms thereof such as the third-person singular form "comprises" and the present participle form "comprising" in the description and the claims are construed as an open and inclusive, meaning "inclusive, but not limited to". In the description, terms such as "one embodiment", "some embodiments", "exemplary embodiments", "example", "some examples", or "specific example" are intended to indicate that specific features, structures, materials or characteristics related to the embodiment(s) or example(s) are included in at least one embodiment or example of the present disclosure. Schematic representations of the above terms do not necessarily refer to the same embodiment(s) or example(s). In addition, the specific features, structures, materials or characteristics may be included in any one or more embodiments or examples in any suitable manner.

Below, terms such as "first" and "second" are only used for a purpose of description, and are not to be construed as indicating or implying the relative importance or implicitly indicating the number of indicated technical features. Thus, a feature defined with "first" or "second" may explicitly or implicitly include one or more of the features. In the description of the embodiments of the present disclosure, term "a/the plurality of" means two or more unless otherwise specified.

In the description of some embodiments, terms "coupled", "connected" and derivatives thereof may be used. For example, the term "connected" may be used when describing some embodiments to indicate that two or more components are in direct physical or electrical contact with each other. For another example, the term "coupled" may be used in the description of some embodiments to indicate that two or more components are in direct physical or electrical contact. However, the term "coupled" or "communicatively coupled" may also mean that two or more components are not in direct contact with each other but still cooperate or interact with each other. The embodiments disclosed herein are not necessarily limited to the content herein.

As used herein, the term if, depending on the context, is optionally construed as "when", "in a case where", "in response to determining", or "in response to detecting". Similarly, depending on the context, the phrase "if it is determined" or "if [a stated condition or event] is detected" is optionally construed as "in a case where it is determined", "in response to determining", "in a case where [the stated condition or event] is detected", or "in response to detecting [the stated condition or event]".

The phrase "applicable to" or "configured to" as used herein indicates an open and inclusive expression, which does not exclude devices that are applicable to or configured to perform additional tasks or steps.

In addition, the phrase "based on" as used herein is meant to be open and inclusive, since a process, step, calculation or other action that is "based on" one or more of the stated conditions or values may, in practice, be based on additional conditions or values beyond those stated.

At present, forms are widely used in various industries. Considering the medical industry as an example, in order to improve the rehabilitation guidance for patients, most hospitals will follow up patients on a regular basis. Especially for patients with chronic diseases, hospitals need to follow up the patients regularly to understand the physical condition of the patients, so as to adjust the treatment plan of the patients. A follow-up form is required for follow-up. The follow-up form contains a plurality of elements that characterize physical health data. For example, as shown in FIGS. 1A and 1B, a follow-up form 100 for patients with chronic hypertension is provided. The name of the follow-up form 100 is "Hypertension Patient Follow-up Service Record Form". The patient is interviewed according to the content of the follow-up form, and relevant health data of the patient is filled in according to the interview result, so as to achieve the purpose of understanding the patient's physical condition. In the related art, some small medical institutions are still in the stage of handwritten medical records and handwritten follow-up forms. For example, health data is handwritten on paper follow-up forms. This kind of paper forms cannot realize data transmission and submission, which is not conducive to the collection and processing of health data.

Figure 13:
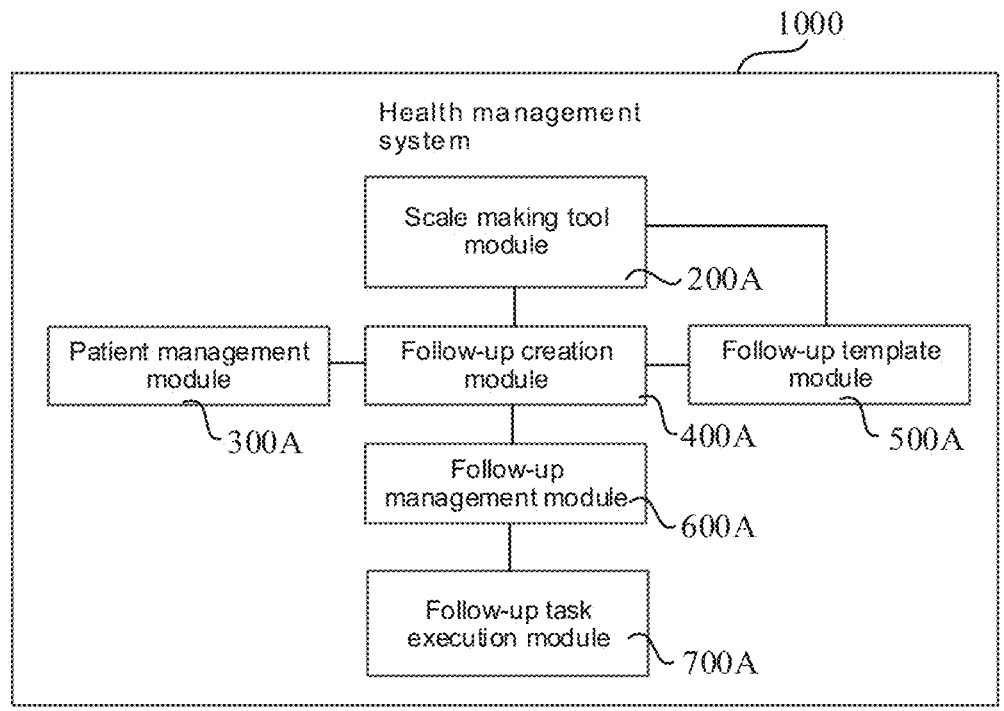
FIG. 13 is a structural diagram of a health management system, according to some embodiments of the present disclosure.

Based on this, as shown in FIG. 13, some embodiments of the present disclosure provide a health management system 1000. The health management system 1000 includes a scale making tool module 200A and a follow-up creation module 400A. The scale making tool module 200A is configured to generate a follow-up form in response to an operation instruction for making the follow-up form. The scale making tool module 200A is connected to the follow-up creation module 400A, and the follow-up creation module 400A is configured to create a follow-up task including the generated follow-up form in response to an operation instruction for creating the follow-up task.

In some embodiments, the health management system 1000 further includes a patient management module 300A, a follow-up template module 500A, a follow-up management module 600A, and a follow-up task execution module 700A. The patient management module 300A is configured to manage the basic information of the patient. The follow-up template module 500A is configured to generate a follow-up template in response to an operation instruction for creating the follow-up template, and the follow-up template includes the generated follow-up form. The follow-up management module 600A is configured to manage the follow-up tasks, and the follow-up task execution module 700A is configured to execute the created follow-up task in response to an operation instruction for executing the follow-up task.

The health management system is applied to an electronic device including a display screen, and relevant interfaces of the health management system can be displayed on the display screen. As shown in FIGS. 2A to 2G, and 4A to 4B, the relevant interfaces of the health management system include a scale making tool interface 200 and a follow-up creation interface 400. When the scale making tool module 200A is run, the scale making tool interface 200 is displayed; when the follow-up creation module 400A is run, the follow-up creation interface 400 is displayed.

In a case where the health management system 1000 further includes the patient management module 300A, the follow-up template module 500A, the follow-up management module 600A and the follow-up task execution module 700A, as shown in FIGS. 3, 5A to 7, the relevant interfaces of the health management system 1000 further include a patient management interface 300, a follow-up template interface 500, a follow-up management interface 600 and a follow-up task execution interface 700. When the patient management module 300A is run, the patient management interface 300 is displayed; when the follow-up template module 500A is run, the follow-up template interface 500 is displayed; when the follow-up management module 600A is run, the follow-up management interface 600 is displayed; and when the follow-up task execution module 700A is run, the follow-up task execution interface 700 is displayed.

Some embodiments of the present disclosure further provide a follow-up form management method applied to the health management system. The method includes the production of the follow-up form and the application of the follow-up form.

Figure 8:
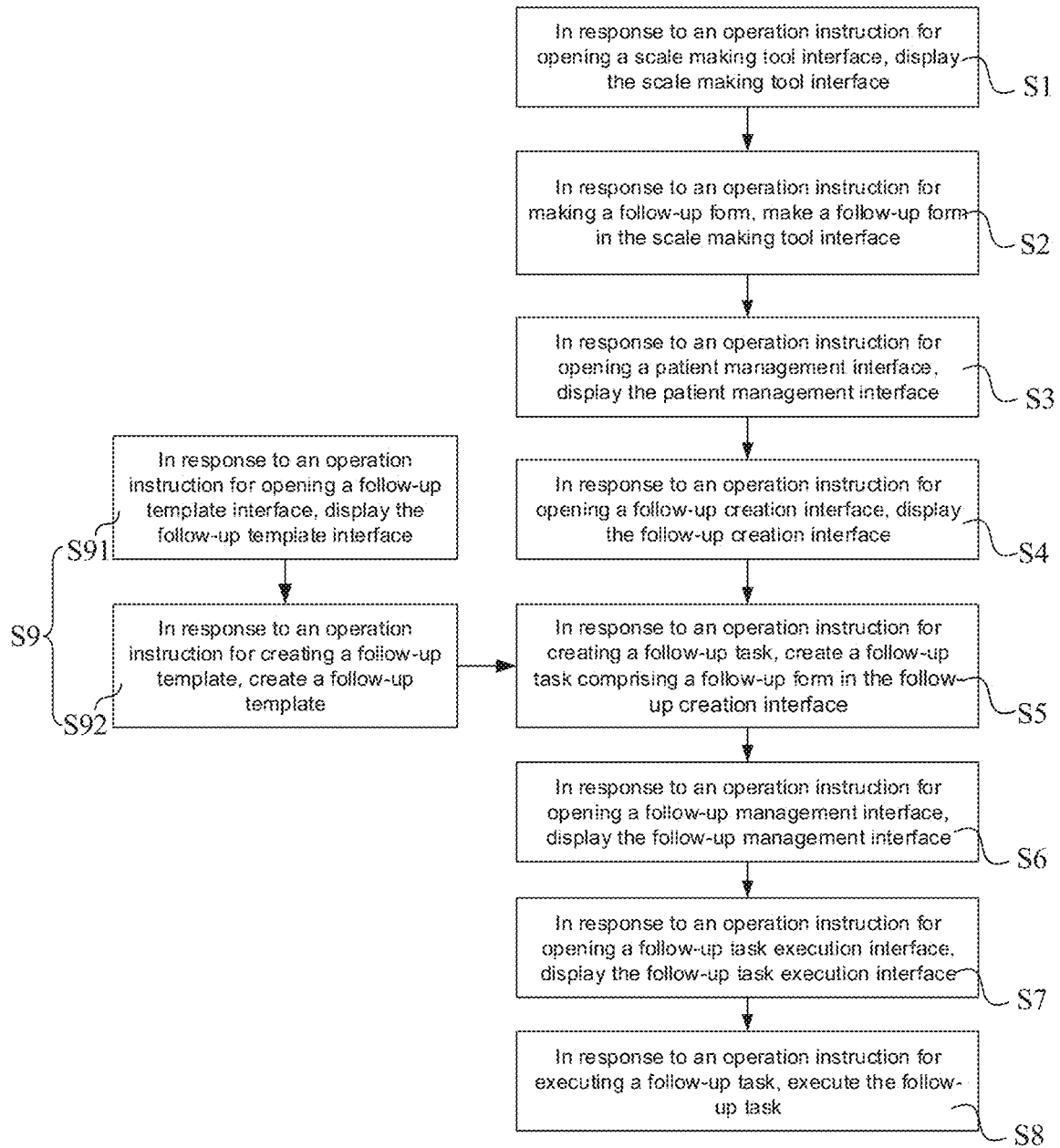
FIG. 8 is a flowchart of a follow-up form management method, according to some embodiments of the present disclosure.

As shown in FIG. 8, firstly, the application of the follow-up form management method in the health management system is briefly introduced below.

In S1, as shown in FIGS. 2A to 2G, in response to an operation instruction for opening a scale making tool interface, the scale making tool interface 200 is displayed. The operation instruction for opening the scale making tool interface is, for example, to select an icon 91, in the left main menu bar 9, corresponding to the scale making tool interface 200.

In S2, in response to an operation instruction for making a follow-up form, the follow-up form is made in the scale making tool interface 200, and the made follow-up form is saved.

Figure 3:
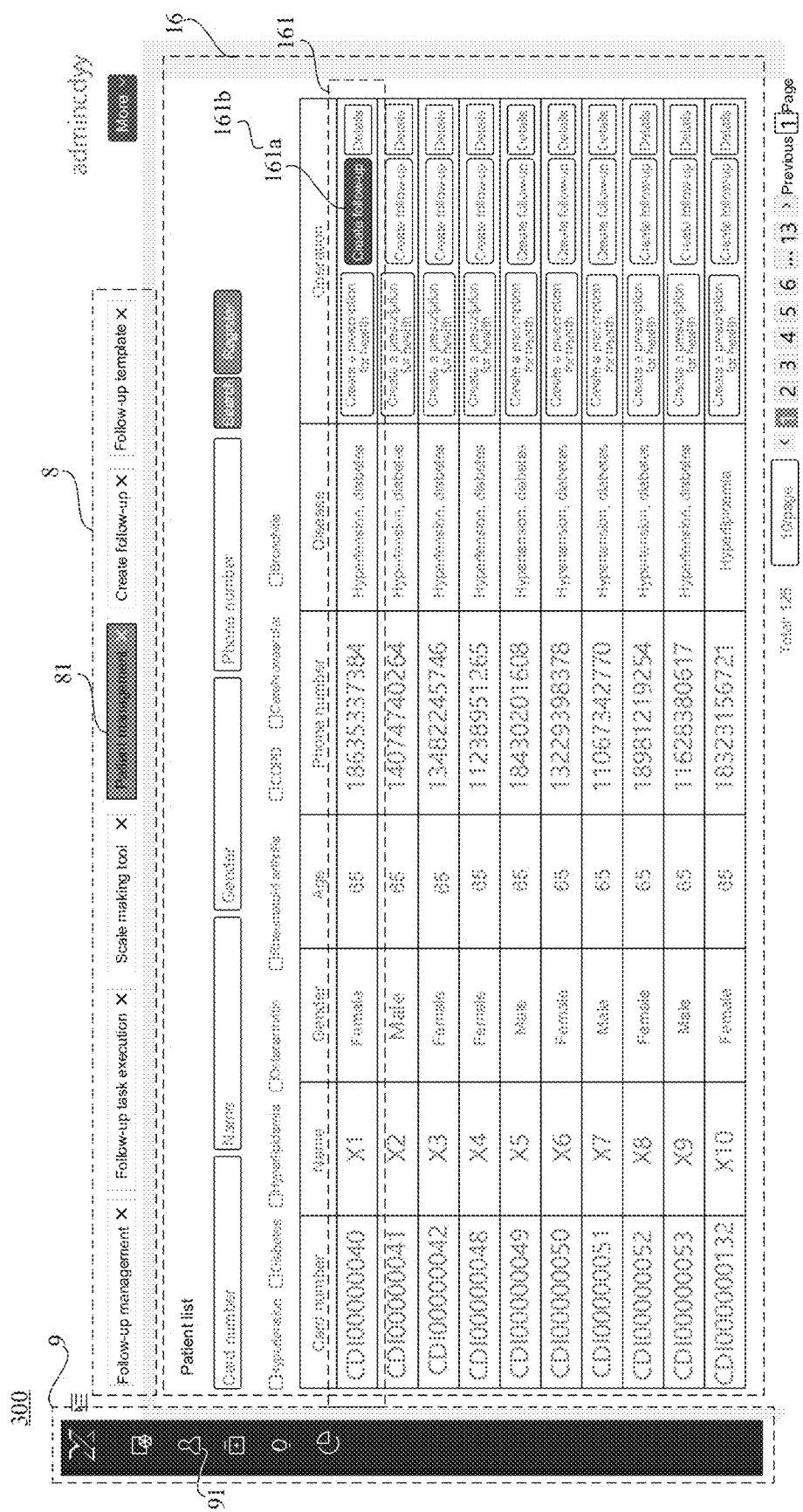
FIG. 3 is a schematic diagram of a patient management interface in a follow-up form management method, according to some embodiments of the present disclosure.

In S3, as shown in FIG. 3, in response to an operation instruction for opening a patient management interface, the patient management interface 300 is displayed. The operation instruction for opening the patient management interface is, for example, to select an icon 91, in the main menu bar 9, corresponding to the patient management interface 300. The patient management interface 300 includes a patient list area 16. The patient list area 16 includes a plurality of patient directories 161. Each patient directory 161 includes basic information of a patient and a corresponding operation index item 161b. The operation index item 161b includes a follow-up creation index item 161a.

Figure 4A:
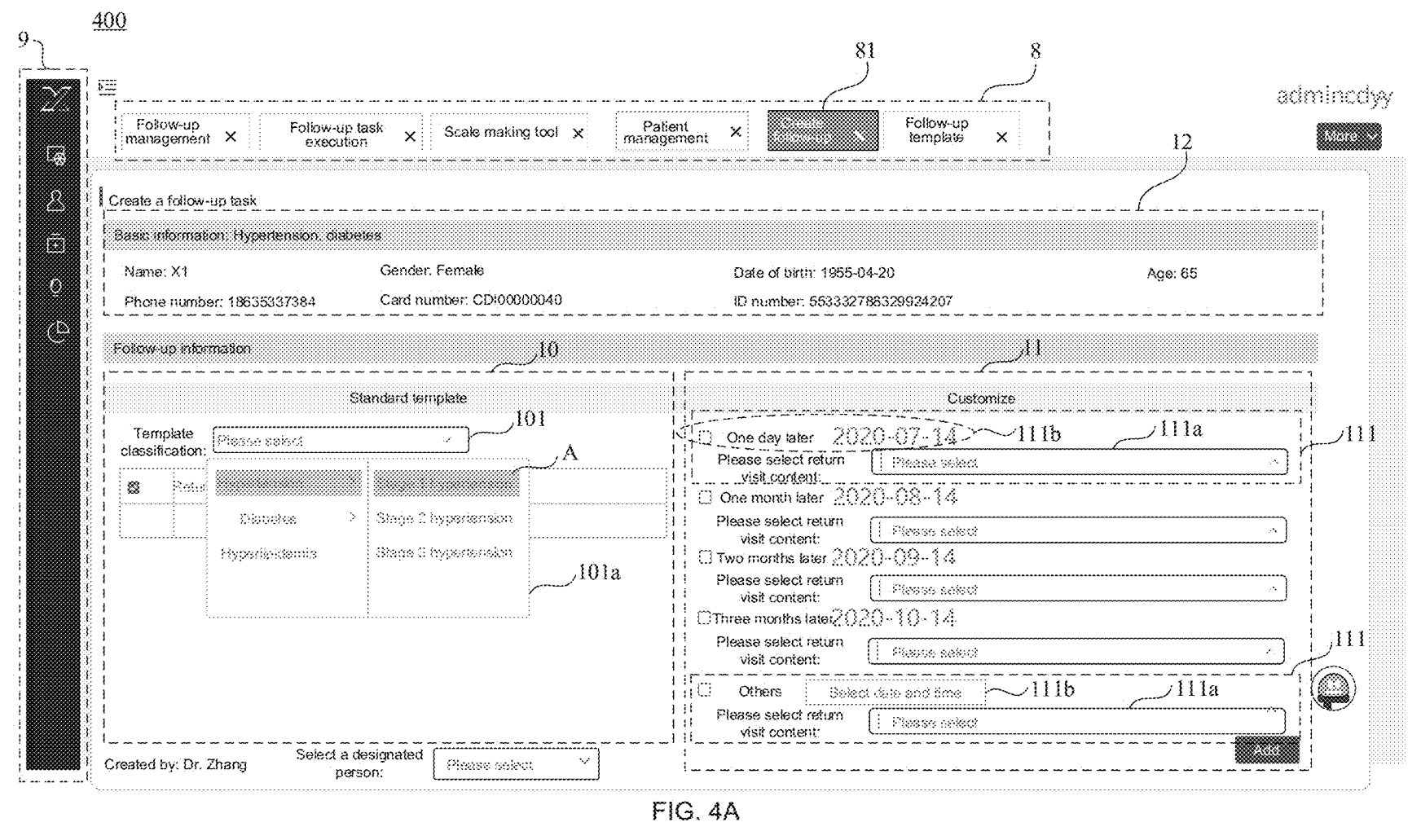
Figure 4B:
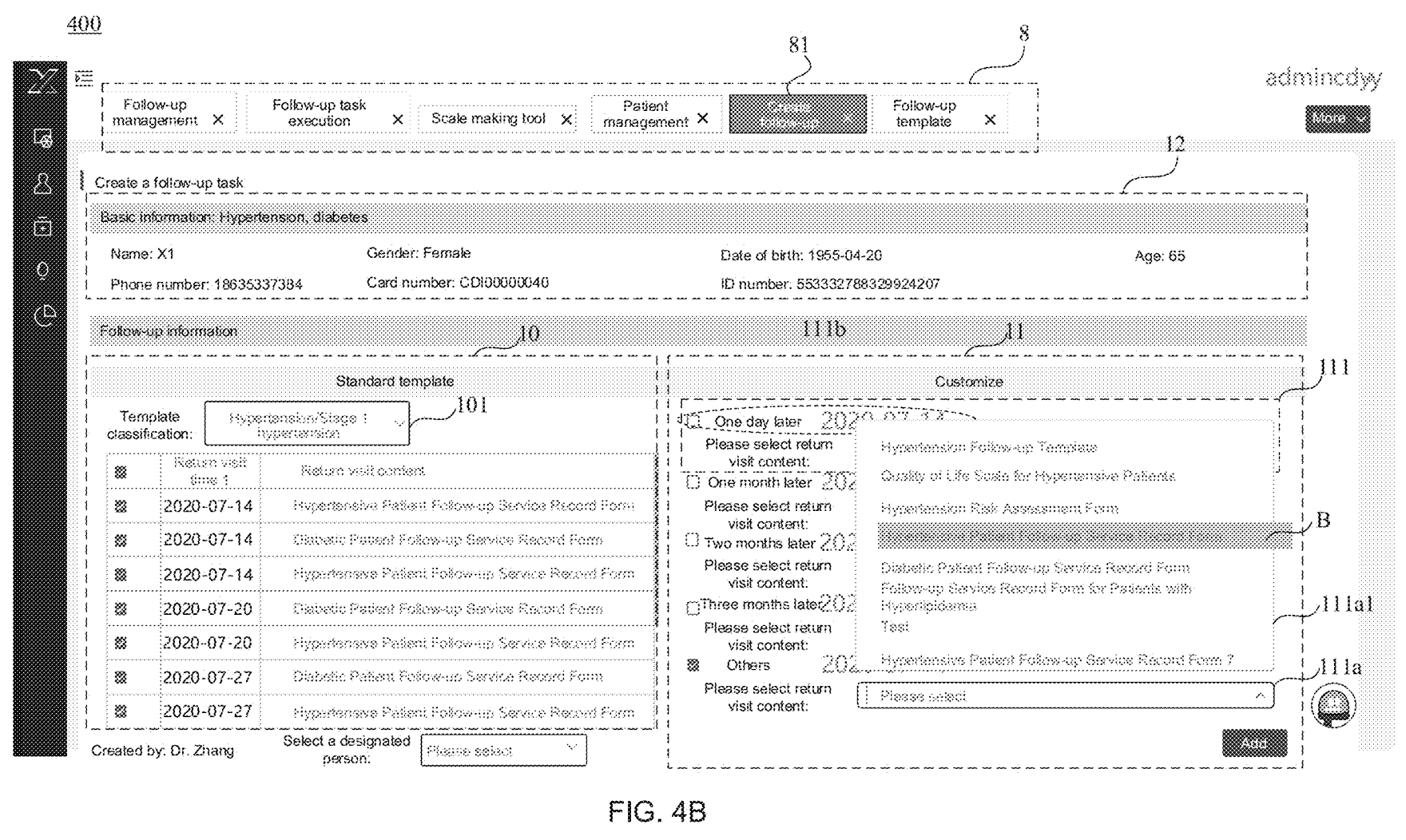

In S4, as shown in FIGS. 4A and 4B, in response to an operation instruction for opening a follow-up creation interface, the follow-up creation interface 400 is displayed. The operation instruction for opening the follow-up creation interface is, for example, to select the follow-up creation index item 161a of a patient in the patient management interface 300, so as to enter the follow-up creation interface 400 corresponding to the patient.

As shown in FIG. 4A, the follow-up creation interface 400 includes an options menu 101a. The options menu 101a includes a plurality of options A corresponding to the generated follow-up form. As shown in FIG. 4B, the follow-up creation interface 400 includes an options menu 111a1. The options menu 111a1 includes a plurality of options B corresponding to the generated follow-up form.

In S5, as shown in FIGS. 4A and 4B, in response to an operation instruction for creating a follow-up task, a follow-up task including a follow-up form is created in the follow-up creation interface 400. The follow-up form included in the follow-up task is the follow-up form corresponding to the option selected from the options menu under the operation instruction for creating the follow-up task. The follow-up task includes return visit content and return visit time, and the return visit content is the content of the corresponding follow-up form.

Figure 6:
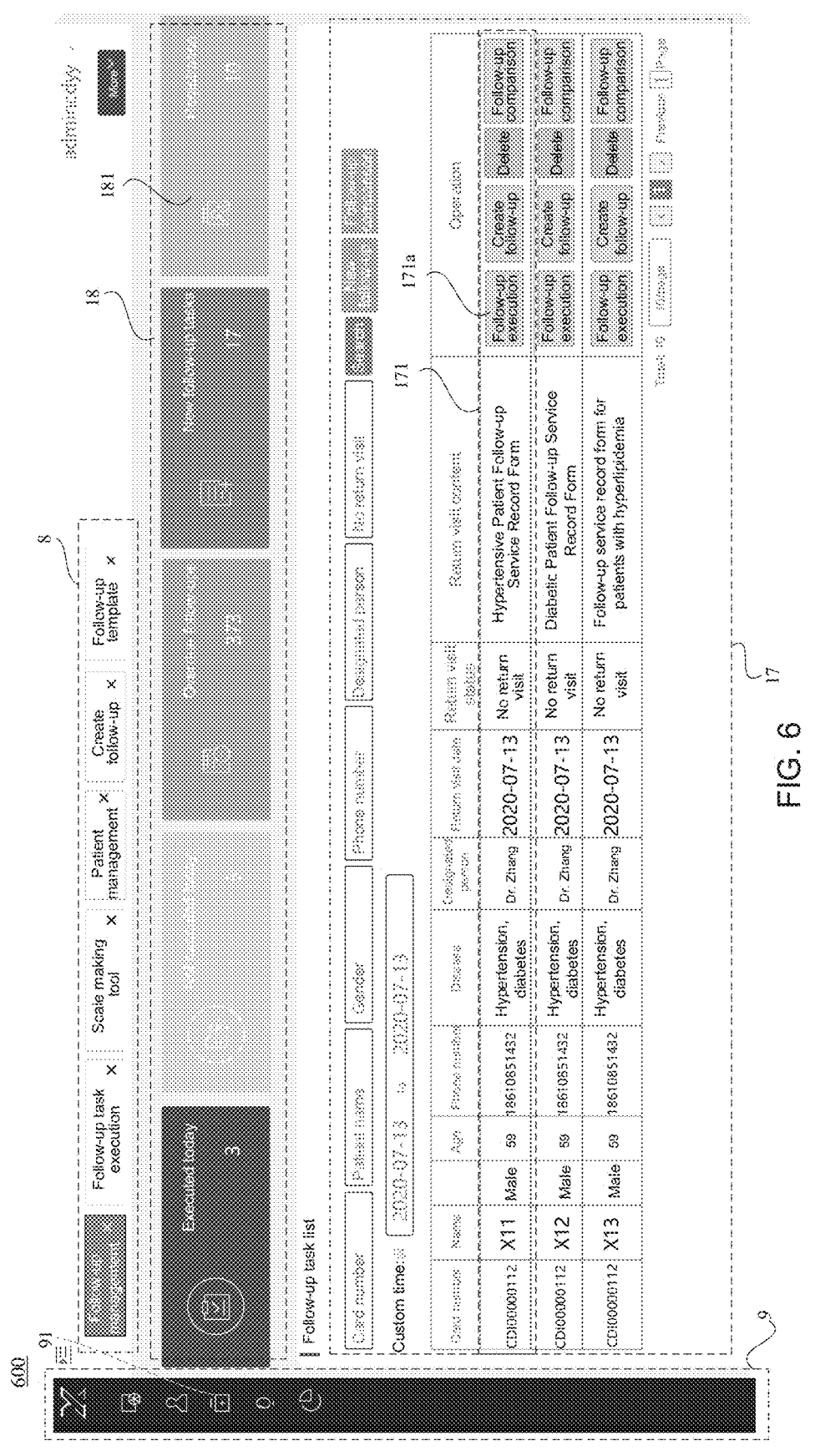

In S6, as shown in FIG. 6, in response to an operation instruction for opening a follow-up management interface, the follow-up management interface 600 is displayed. The operation instruction for opening the follow-up management interface is, for example, to select an icon 91 in the main menu bar 9, corresponding to the follow-up management interface 600.

The follow-up management interface 600 includes a follow-up task list area 17, and the follow-up task list area 17 includes a plurality of follow-up task directories 171. Each follow-up task directory 171 includes the basic information and follow-up information of the patient, and corresponding operation index items 171*a*. The operation index items 171*a* include a follow-up execution index item.

Figure 7:
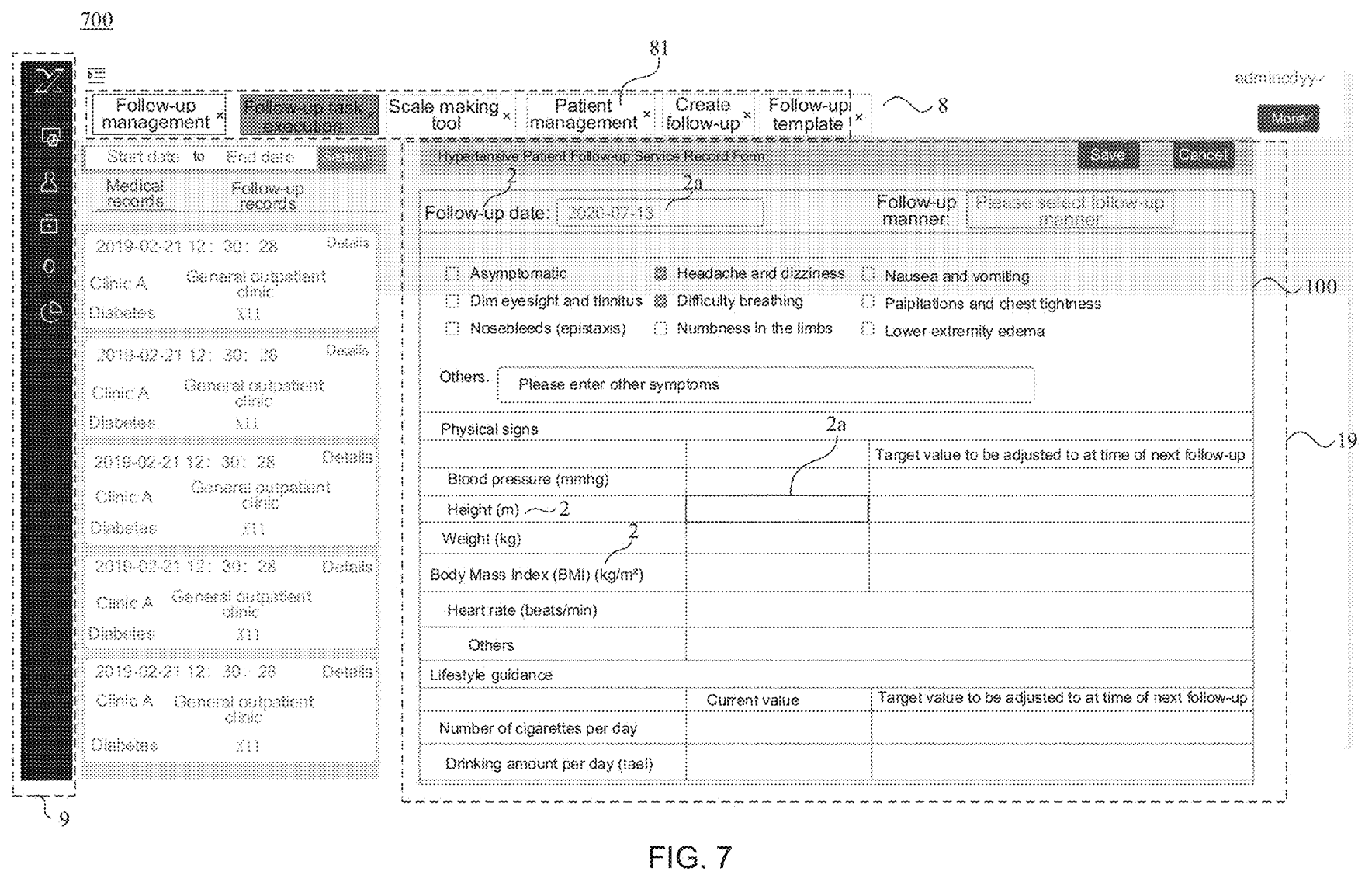

In S7, as shown in FIG. 7, in response to an operation instruction for opening a follow-up task execution interface, the follow-up task execution interface 700 is displayed. The operation instruction for opening the follow-up task execution interface is, for example, to select a follow-up execution index item 171*a* of a follow-up task directory 171 in the follow-up management interface 600, so as to enter the follow-up task execution interface for the patient. The follow-up task execution interface 700 includes a follow-up task execution area 19, and the follow-up task execution area 19 displays a follow-up form 100 corresponding to the follow-up task.

In S8, as shown in FIG. 7, in response to an operation instruction for executing a follow-up task, the follow-up task is executed. The operation instruction for executing the follow-up task is, for example, to fill in the follow-up form 100 according to the follow-up of the patient, so that after the blank form 100 shown in FIG. 1A is filled out, it becomes the follow-up form 100 with the recorded health data in FIG. 1B.

In some embodiments, as shown in FIG. 6, the operation index items 171*a* of each follow-up task directory 171 in the follow-up management interface 600 further include a follow-up creation index item. The operation instruction for opening the follow-up creation interface in S4 may also be to select the follow-up creation index item of a patient in the follow-up management interface 600, so as to enter the follow-up creation interface 400 corresponding to the patient.

It will be noted that, each of the above interfaces includes a navigation pane 8, and the navigation pane 8 includes a plurality of interface tabs 81. Each interface tab 81 corresponds to an interface currently displayed by the health management system.

Some embodiments of the present disclosure provide a follow-up form management method applied to a health management system. With the follow-up form management method, a user can create a follow-up form, create a follow-up task, and execute a follow-up task, thereby making it more convenient to provide follow-up services to patients and collects patients' health data systematically. Compared with handwritten follow-up forms, it simplifies the workload of doctors and improves work efficiency; moreover, the application system collects and saves health data, which makes it easier to grasp the patient's health status and improve the treatment effect of patients.

Figure 9:
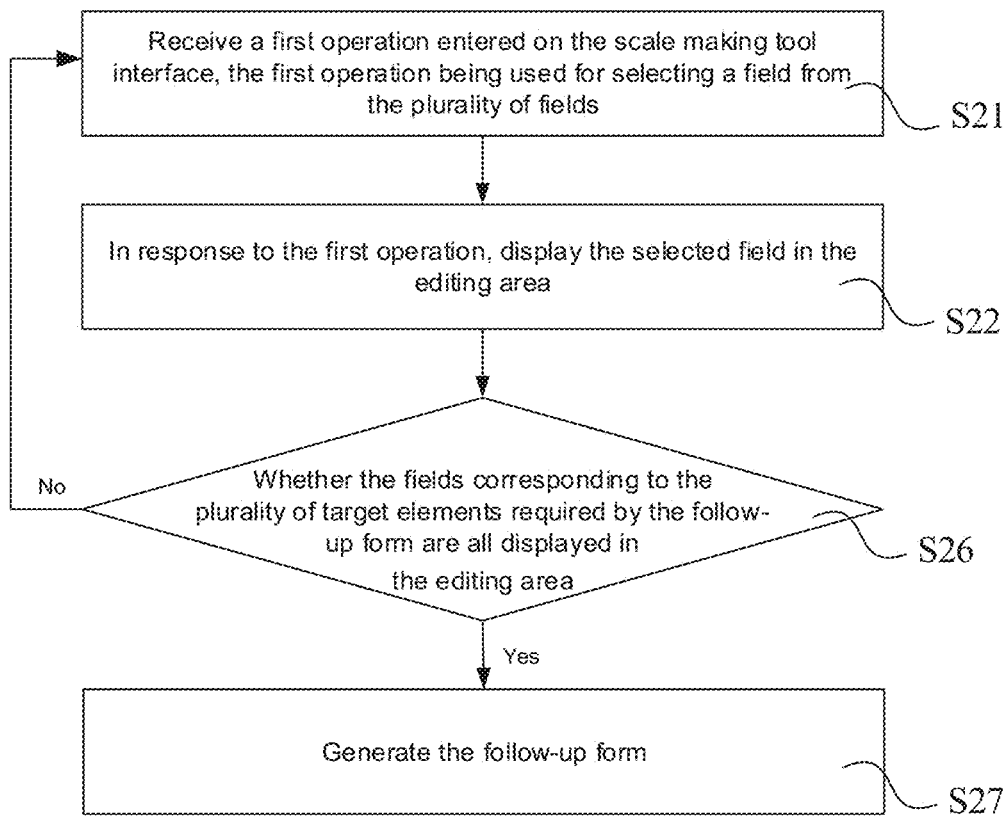
FIG. 9 is another flowchart of a follow-up form management method, according to some embodiments of the present disclosure.

As shown in FIG. 9, the steps of making the follow-up form 100 in S2 will be introduced in detail below.

Referring to FIGS. 2A to 2E, the scale making tool interface 200 includes a field display area 3 and an editing area 4. The field display area 3 includes a plurality of fields 31, and the editing area 4 is used for making the follow-up form 100. The follow-up form 100 to be made includes a plurality of target elements, and each target element is generated by a field.

It will be noted that the follow-up form 100 includes a plurality of "elements", and the "elements" refer to the basic components of the follow-up form 100, which are essentially the carriers of various information or data in the follow-up form 100. Information of follow-up subjects (patients) is collected through the elements. The "target element" refers to the "element" to be generated in the follow-up form 100 to be made (that is, the carrier of the information or data to be generated). The "field" included in the field display area 3 refers to the basic component used to generate the "target element", and the "field" can be understood as the unedited initial state of the "target element".

For example, the follow-up form 100 shown in FIG. 1A includes a header 1 and a plurality of elements 2. The header 1 is the title of the form 100. The follow-up form 100 includes a "Follow-up date" element, a "Follow-up manner" element, and a "Symptoms" element, a "Body mass index" element, etc. These elements are the basic components of the follow-up form 100. For example, the "Body mass index" element is the carrier of the body mass index data of the follow-up subject. Each element has set properties, and the properties represent the properties or characteristics of the element. The properties are configured to define the name of the target element, the fill-in settings, the data source, and other characteristics. If the follow-up form to be made is the follow-up form 100 shown in FIG. 1A, the target elements are the elements to be generated in the follow-up form 100 to be made, that is, the "Follow-up date" element, the "Follow-up manner" element, the "Symptoms" element, the "Body mass index" element, and other elements to be generated.

Figure 2B:
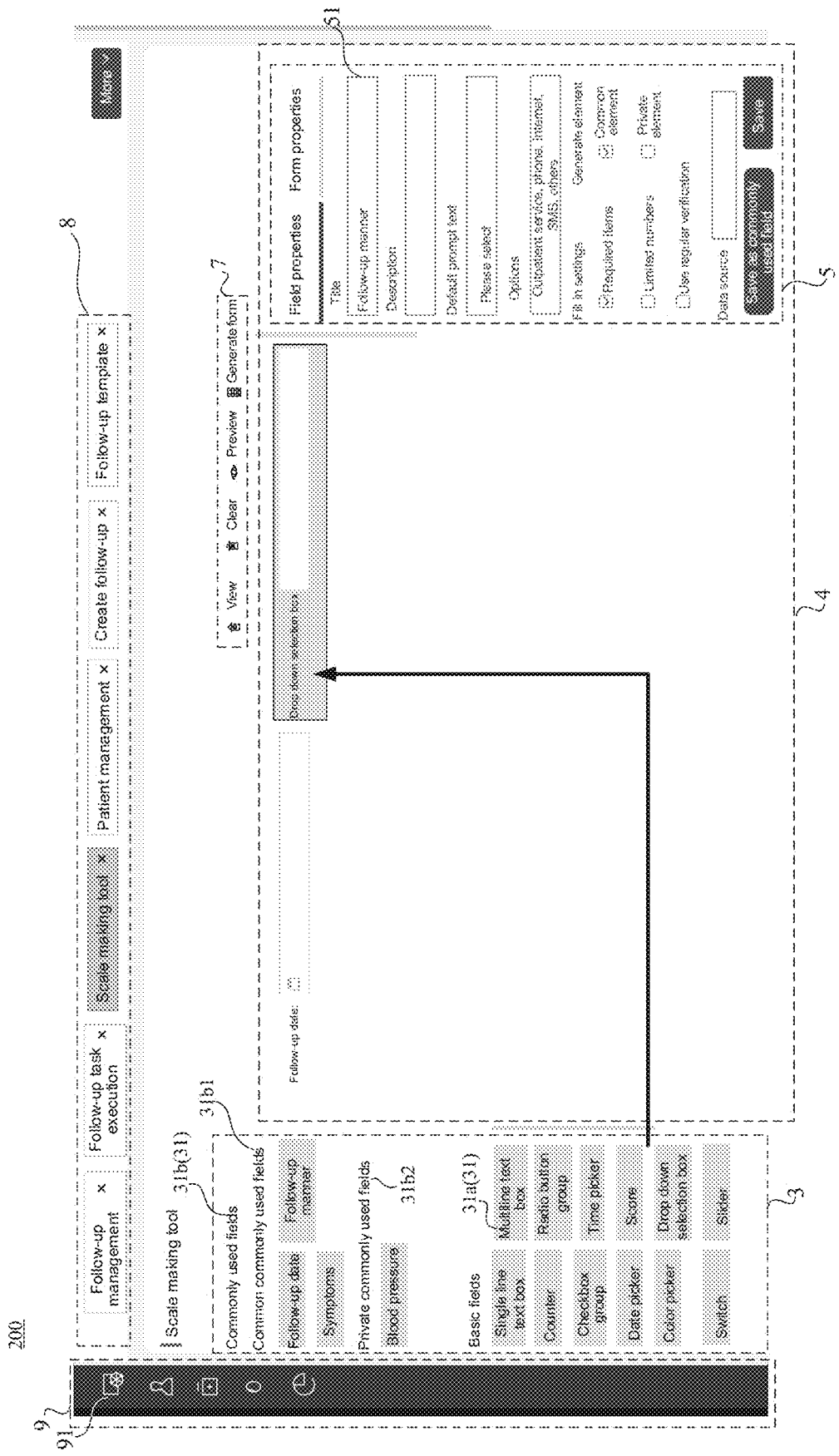
FIG. 2B is another schematic diagram of a scale making tool interface in a follow-up form management method, according to some embodiments of the present disclosure.

For example, as shown in FIGS. 2A and 2B, the fields 31 include basic fields 31*a*; alternatively the fields 31 include basic fields 31*a* and commonly used fields 31*b*, which will be introduced later.

The follow-up form 100 in FIG. 1A can also be understood as a follow-up form made by using the method of making the follow-up form 100 in S2. The form includes a plurality of elements 2. Each element 2 in the form 100 shown in FIG. 1A includes an edit box. If the box is empty, it means that the element is in a state with no content filled; that is, the content of the element is empty. For example, the specific date is not filled in the edit box of the "Follow-up date" element, the specific manner is not filled in the edit box of the "Follow-up manner" element, the plurality of symptoms are not filled in the edit box of the "Symptoms" element, multiple symptoms are not checked in the edit box of the "Symptoms" element, and the edit box of the "Body mass index" element is empty. That is to say, after the follow-up form 100 is created, the content of each element 2 is to be filled in, and the user needs to fill in the edit boxes of all elements 2 of the form 100, so as to realize the collection of health data, FIG. 1B shows a state in which the edit boxes of all elements in the made follow-up form are filled in (that is, the data collection is completed). For example, the edit box of the "Follow-up manner" element is filled with "Outpatient", the options of "Headache and dizziness" and "Nausea and vomiting" are checked in the edit box of the "Symptoms" element, and the edit box of the "Body mass index" element is filled in with "28.9". For example, the follow-up form 100 shown in FIG. 1B may be considered as a follow-up form 100 of the content of the elements filled in according to the follow-up result after a doctor performs a follow-up service for a hypertensive patient (that is, after a follow-up task is executed).

In the embodiments of the present disclosure, the user who makes the follow-up form 100 is called the first user, and the user who fills in the content of each element 2 of the follow-up form 100 is called the second user. That is, the user who executes the follow-up task is the second user. In an example where the form 100 is a Hypertensive Patient Follow-up Service Record Form, the first user may be, for example, a doctor, a nurse, an operation manager, etc., and the second user may be, for example, a doctor, a nurse, or a patient. For example, the first user and the second user may be the same person or may not be the same person.

In S1, the scale making tool interface 200 is displayed first, and the first user creates a form in the scale making tool interface 200. In the scale making tool interface 200, the plurality of fields 31 are configured to generate the target elements, and the editing area 4 is used for creating a form. At the beginning of creating a new form, the content of the editing area 4 is, for example, empty.

Figure 2C:
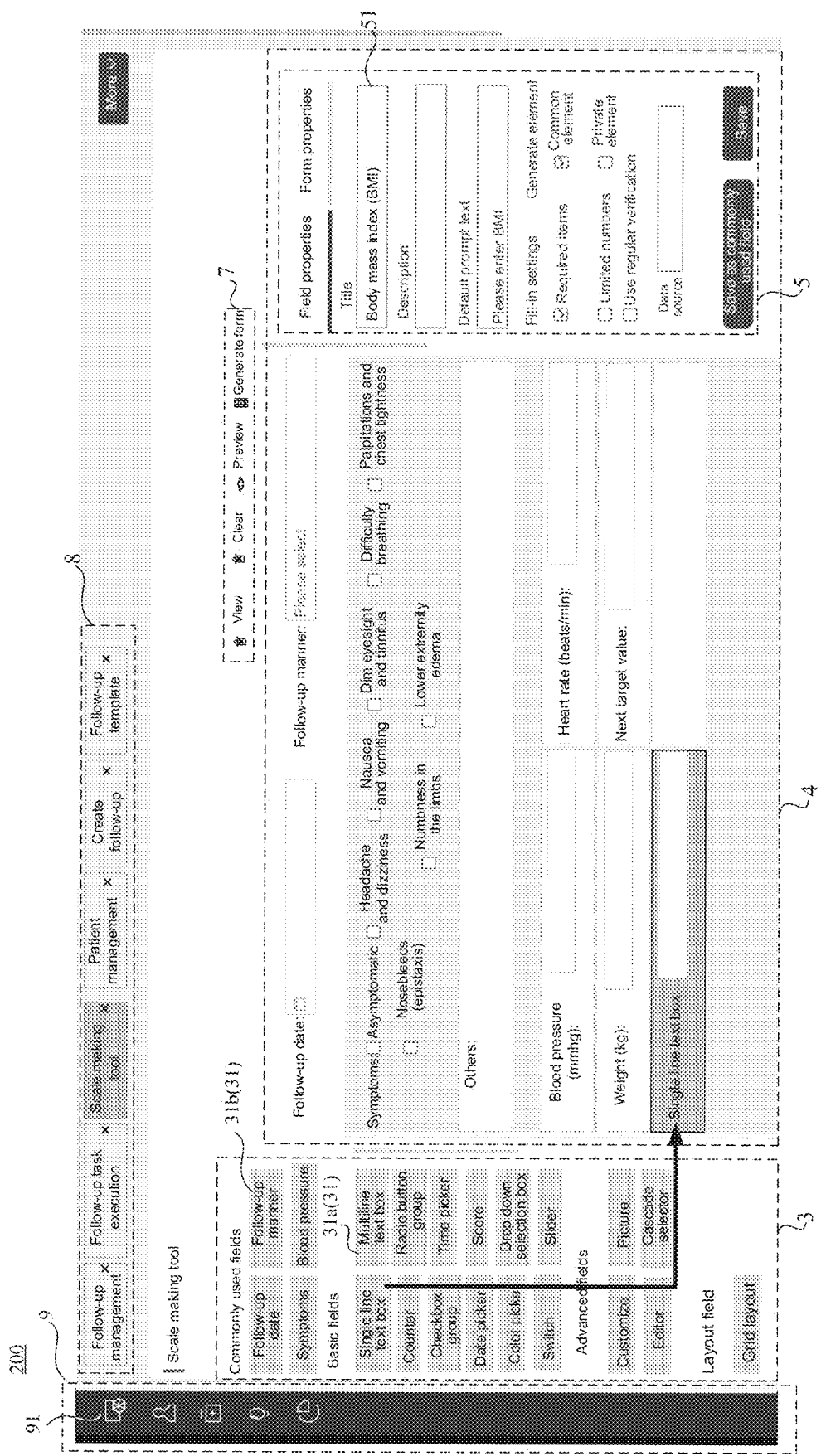
FIG. 2C is yet another schematic diagram of a scale making tool interface in a follow-up form management method, according to some embodiments of the present disclosure.

In S21, as shown in FIGS. 2B and 2C, a first operation entered on the scale making tool interface 200 is received. The first operation is used for selecting a field 31 from the plurality of fields 31.

It will be noted that the "first operation to the Nth operation" involved in the embodiments of the present disclosure all refer to operations performed by the user. For example, the "first operation to the Nth operation" may be clicking, double-clicking, dragging, or other operations with a mouse, or may be in the form of a touch on the screen, a gesture, voice, etc.

For example, in S21, the first operation is to select a field 31 from the plurality of fields 31 by double-clicking with the mouse, and click a target position in the editing area 4 with the mouse, so that the field 31 is displayed at the target position in the editing area 4. Alternatively, the first operation is to select a field 31 from the plurality of fields 31, and drag the field 31 to the target position in the editing area 4. The selected field 31 is, for example, a single line text box.

In S22, as shown in FIGS. 2B and 2C, in response to the first operation, the selected field 31 is displayed in the editing area 4.

For example, in response to the first operation, the selected field 31 is displayed at the target position of the editing area 4. For example, a drop-down selection box is displayed at the target position of the editing area 4.

It will be noted that, since each target element 2 in the follow-up form 100 to be made is generated by a single field 31, after the selected field 31 is displayed in the editing area 4, operations (e.g., S23' to S25) as described later in the embodiments of the present disclosure need to be further performed on the field 31, so as to use the field to generate the corresponding target element. For example, as shown in FIG. 2B, at the target position in the upper right corner of the editing area 4, the target element generated by the drop-down selection box is the "Follow-up manner" element.

In S260, the first operation is received and responded to repeatedly, until fields 31 corresponding to the plurality of target elements required by the follow-up form to be made are all displayed in the editing area 4, so as to generate the follow-up form 100.

For example, as shown in FIG. 9, the above S260 is: S26, determining whether the fields 31 corresponding to the plurality of target elements required by the follow-up form are all displayed in the editing area 4. If not, return to S21, and continue the operations of S21 and S22; if yes, then proceed to S27 (generating the follow-up form).

For example, in the follow-up form to be created, the included target elements include 20 target elements such as the "Follow-up date" element, the "Follow-up manner" element, and the "Symptoms" element. By repeating the operations of S21 and S22, 20 fields 31 are selected in sequence in the field display area 3, and the fields 31 are displayed in the editing area 4 in sequence, so as to generate the corresponding target elements 2, and in turn, to generate the required form 100.

Through the method of making the follow-up form in the follow-up form management method provided by some embodiments of the present disclosure, the user can complete the design and production of the form according to his n needs, and can customize the content of the form through corresponding operations, with high flexibility. In this way, the form making efficiency may be improved, and the software operation and maintenance costs may be reduced.

In some embodiments, as shown in FIGS. 2A to 2D, the plurality of fields 31 include at least one basic field 31*a*, and the basic field 31*a* includes at least one property to be edited.

Herein, the "basic field" is the basic component used to generate the target element that has not been edited. The basic field is, for example, a basic component preset by the software engineer of the health management system. After the properties of the basic field 31*a* are edited and saved, the basic field 31*a* generates the target element. The "properties" represent the properties or characteristics of an element, and the "properties" are configured to define the names, fill-in settings, data sources, and other features of the elements or fields. The "properties to be edited" refer to items that need to be edited in the basic fields.

For example, as shown in FIGS. 2B and 2C, the field display area 3 of the scale making tool interface 200 includes a plurality of basic fields 31*a*. For example, the plurality of basic fields 31*a* are a single line text box, a multiline text box, and a checkbox group, a radio button group, a drop-down selection box, a multi-level drop-down box, a time picker, a date picker, a color picker, etc. Each basic field 31*a* includes at least one property to be edited, and different basic fields 31*a* include different properties. For example, the properties of a single line text box include a title property, a description property, a default prompt text property, a fill-in setting property (whether it is required, whether there is a word limit, whether there is a regular check, etc.), a data source property, etc. The is properties of date and time include a title property, a description property, a data type property (date, time, or date+time), a title time displayed by default property, a fill-in setting property (the fill-in setting property includes whether it is required, whether to limit the optional range of dates, whether it can be input, etc.), a data source property, etc. By displaying the properties menu 5 corresponding to each basic field 31*a* in the editing area, and by filling in the content of the property edit boxes 51 in the properties menu 5, the properties of the basic field may be edited. Before the properties of the basic field 31*a* are edited, the property edit boxes in the properties menu 5 of the basic field 31*a* are blank.

Figure 10A:
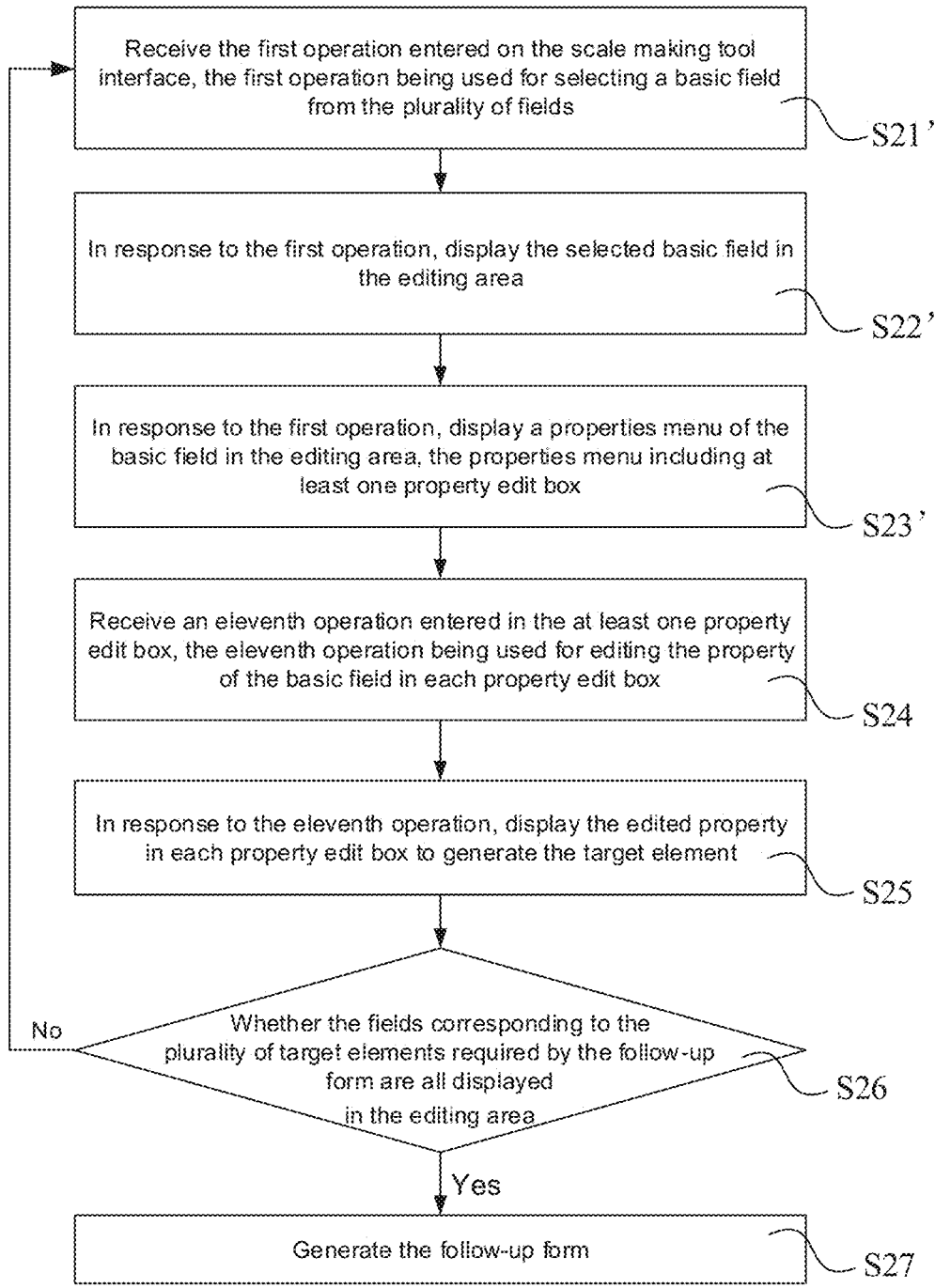
FIG. 10A is yet another flowchart of a follow-up form management method, according to some embodiments of the present disclosure.

As shown in FIG. 10A, in a case where the field 31 selected by the first operation is a basic field 31*a* the above S21 is: S21', receiving the first operation entered on the scale making tool interface 200, the first operation being used for selecting a basic field 31*a* from the plurality of fields 31. The above S22 is: S22', in response to the first operation, displaying the selected basic field 31 in the editing area 4. For example, as shown in FIG. 2C, the selected basic field 31*a* is a single line text box, and the selected single line text box is displayed in the editing area 4.

In the above case, after S22', the step of making the follow-up form 100 in S2 further includes S23' to S25.

In S23', in response to the first operation, the properties menu 5 of the basic field 31*a* is displayed in the editing area 4. The properties menu 5 includes at least one property edit box 51.

For example, as shown in FIG. 2C, in response to the first operation, the properties menu 5 of the single line text box is displayed in the editing area 4. The first operation may be, for example, to double-click the single line text box displayed in the editing area 4. That is to say, the first operation includes an operation of selecting the single line text box with the mouse and dragging the single line text box to the target position of the editing area 4, and an operation of double-clicking the single line text box displayed in the editing area 4. Alternatively, after the single line text box is dragged to the target position in the editing area 4, the properties menu 5 of the single line text box is automatically displayed, and there is no need to perform a double-click operation.

The properties menu 5 includes at least one property edit box 51. For example, at least one property of the single line text box includes a title property, a description property, a default prompt text property, a fill-in setting property (whether it is required, whether there is a word limit, whether there is a regular check, etc.), a data source property, etc.; then, the properties menu 5 includes a title property edit box 51, a description property edit box 51, a default prompt text property edit box 51, a fill-in setting property edit box 51, etc. At this time, the plurality of property edit boxes 51 displayed in the properties menu 5 are all empty, and are in a state to be edited.

In S24, an eleventh operation entered in the at least one property edit box 51 is received, the eleventh operation being used for editing the property of the basic field in each property edit box 51.

For example, the eleventh operation may be an operation of the first user using a mouse to click on a property edit box 51 to select it, and using a keyboard to input corresponding content in the property edit box 51.

In a case where the selected basic field 31*a* is a drop-down selection box, as shown in FIG. 2B, for example, if the title property edit box 51 in the properties menu 5 of the drop-down selection box is filled in with "Follow-up manner", then the target element to be generated by the drop-down selection box will be the "Follow-up manner" element. The default prompt text property edit box 51 is filled in with "Please select", and the options property edit box 51 is filled in with "Outpatient service, phone, Internet, SMS, others". The description property is used for specifying some additional descriptions to the basic field 31*a*, and the description is generally used to instruct the second user to fill in the form 100, and the additional descriptions may not be filled in. For example, no content is filled in the description property edit box 51 here. The fill-in setting property includes whether it is required, whether there is a word limit, whether there is a regular check, etc. The corresponding content may be checked. For example, if the check box corresponding to the required item is checked, it means that in the generated form, the target element is an element that the second user must fill in. The "data source property" refers to a property that the generated element is linked to the data source, and this property enables the content of the element to be automatically generated when filling in the content of the element. The data source refers to a mathematical formula, a mapping relationship, a background database, etc. Here, for example, the data source is not bound; that is, the content of the data source property is not set.

In the case where the selected basic field 31*a* is the single line text box, as shown in FIG. 2C, for example, the title property edit box 51 in the properties menu 5 of the single line text box is filled in with "Body mass index", then the target element to be generated by the single line text box is the "Body mass index" element. The default prompt text property edit box 51 is filled in with "Please entered body mass index". The description property edit box 51 is not filled in with content. The fill-in setting property includes whether it is required, whether there is a word limit, whether there is a regular check, etc. The boxes corresponding to the required fields are checked. The data source property represents some related information linked to the target element generated by the commonly used field 31*b*, and the content of the element can be directly obtained according to the data source property. For example, the calculation formula of body mass index may be filled in the data source property edit box 51. Then, when the second user fills in the content of the form 100, if the patient's height and weight are known, the system mill automatically determine the patients body mass index according to the filled height, weight, and the bound calculation formula of the body mass index, and display the patients body mass index in the edit box of the "Body mass index" element of the follow-up form 100.

In S25, in response to the eleventh operation, the edited property in each property edit box 51 is displayed to generate a target element.

After the first user edits the property in each property edit box 51 of the basic field 31*a* through the eleventh operation, in response to the eleventh operation, the edited property is displayed in each property edit box 51. For example, in FIG. 2C, the text "Body mass index" is displayed in the title property edit box 51 in the properties menu 5 of the single line text box, and the text "Please enter body mass index" is displayed in the default prompt text property edit box 51. Then, the target element is generated by the basic field 31*a* the content of the property of which has been set. As shown in FIGS. 2B and 2C, for example, the "Follow-up manner" element is generated by the drop-down selection box, and the "Body mass index" element is generated by the single line text box.

Figure 2D:
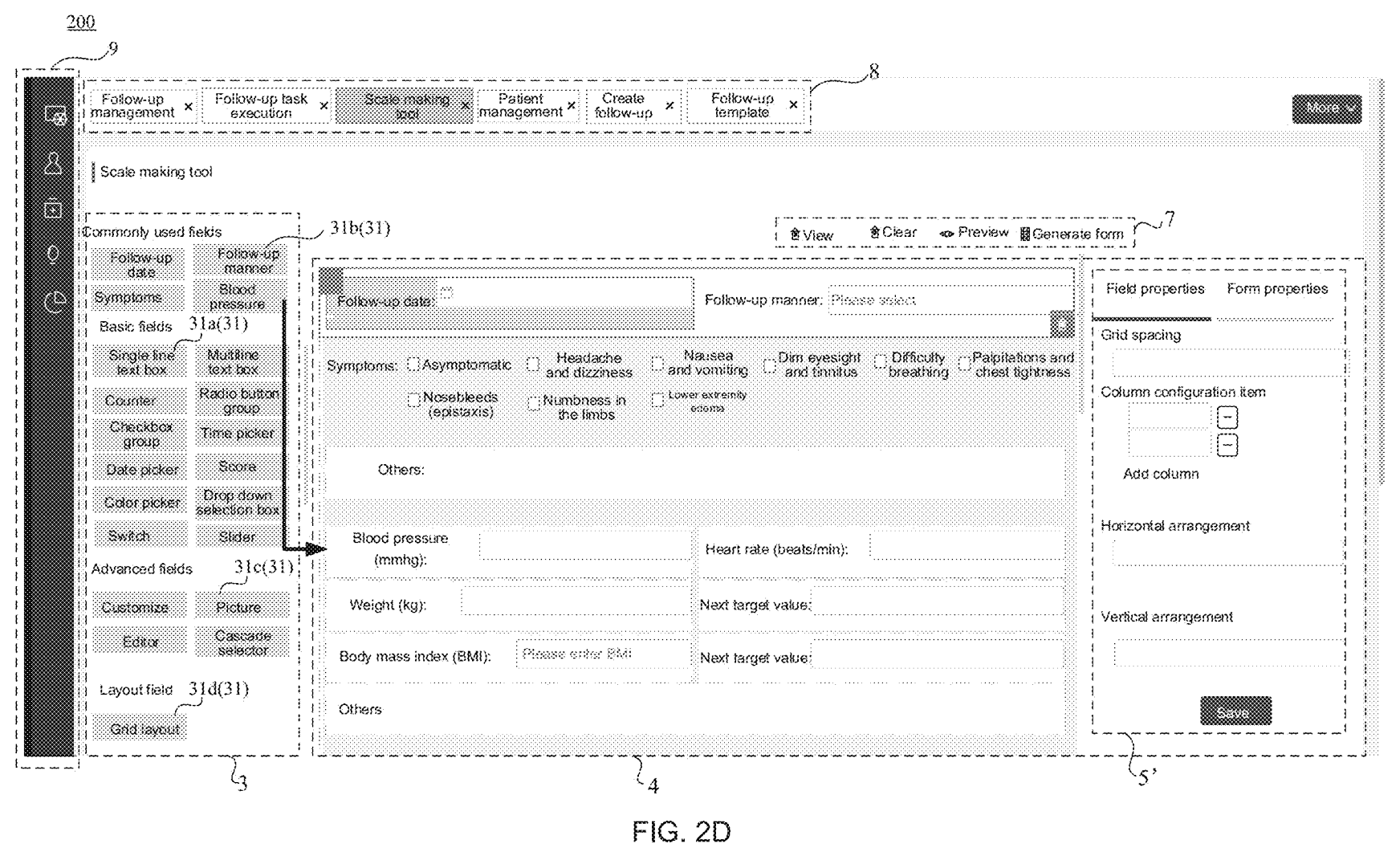

In some embodiments, as shown in FIGS. 2B to 2D, the properties menu 5 further includes a save button. The eleventh operation is used for editing the properties of the basic field in each property edit box 51; in addition, it is also used for selecting the save button to save the edited property to generate the target element.

In some embodiments, as shown in FIGS. 2B and 20, the properties menu 5 further includes a save as commonly used field button. The follow-up form management method further includes a step of saving the target element as a commonly used field 31*b* after the target element is generated, and the step includes S25-1 and S25-2.

In S25-1, a twelfth operation entered in the properties menu is received, the twelfth operation being used for selecting the save as commonly used field button.

For example, as shown in FIGS. 28 and 20, the properties menu 5 of the basic field 31*a* includes the save button and the save as commonly used field button, and the twelfth operation is the operation performed by the first user. For example, after generating the target element by the basic field 31*a* in S25, the user clicks the save as commonly used field button to save the generated target element as a commonly used field 31*b*.

In S25-2, in response to the twelfth operation, the generated target element is displayed in the field display area 3 as a commonly used field 31*b*.

As shown in FIGS. 2B and 2C, the field display area 3 includes a plurality of basic fields 31*a* and a plurality of commonly used fields 31*b*, and the commonly used fields 31*b* include at least one edited property. For example, after the above S21', S22', S23' and S24 are performed on the single line text box, the properties of the single line text box are set, and the "Follow-up manner" element is generated. That is, the target element is generated by the basic field 31*a*, In response to the twelfth operation, the target element is saved as a commonly used field 31b, and the "Follow-up manner" commonly used field is displayed in the field display area 3.

In the embodiments of the present disclosure, the basic field 31a includes at least one property to be edited, the commonly used field 31b includes at least one edited property, and the target element 2 includes at least one edited property. The properties are, for example, a title property, a description property, a default prompt text property, a fill-in setting property, a data source property, etc. Here, "Data source" means the source of the content of the element, or the source of the data collected by the element. For example, for the "Body mass index" element, the "Data source" is obtained according to the height, weight, and the corresponding relationship between the height, weight and body mass index. The "data source property" refers to a property that the generated element is linked to the data source. This property enables the content of the element to be automatically generated when filling in the content of the element. The data source refers to a mathematical formula, a mapping relationship, a background database, etc. There are some embodiments below as to the manner of setting the data source property included in the basic field 31a.

In some embodiments, the plurality of fields include at least two basic fields, and the at least two basic fields include a first basic field and a second basic field(s); the first basic field 31a is used for generating a first target element, the second basic field(s) are used for generating second target element(s), respectively, and a corresponding relationship exists between the first target element and the second target element(s). At least one property edit box of the first basic field includes a data source property edit box.

For example, the first basic field is a single line text box, the second basic fields are each a single line text box, and the number of the second basic fields is two. The first target element generated by the first basic field is, for example, the "Body mass index" element. The second target element generated by one second basic field is the "Height" element, and the second target element generated by the other second basic field is the "Weight" element. The corresponding relationship between body mass index and height and weight is $B=W/H^2$, where B is the body mass index (BMI), W is the weight is (measured by a unit of kg), and H is the height (measured by a unit of m). Then, the above corresponding relationship exists between the "Body mass index" element, the "Height" element and the "Weight" element.

Alternatively, the first basic field is a single line text box, and the second basic field is a single line text box; the first target element generated by the first basic field is, for example, the "Age" element, and the second target element generated by the second basic field is the "Date of birth" element. The corresponding relationship between age and date of birth is: $T=T1-T2$, where T is the age, T1 is the current date, and T2 is the date of birth. Then the above corresponding relationship exists between the "Age" element and the "Date of birth" element.

For another example, the first basic field is a single line text box, and the second basic field is a single line text box; the first target element generated by the first basic field is, for example, the "Expected date of delivery" element, and the second target element generated by the second basic field is the "Last menstrual period" element. The corresponding relationship between the expected date of delivery and the last menstrual date is: the expected delivery date is the month of the last menstrual date plus 9 months or minus 3 months, and plus 7 days. Then the above corresponding relationship exists between the "Expected date of delivery" element and the "Last menstrual date" element.

In the above S24, the eleventh operation entered in at least one property edit box 51 is received, and the eleventh operation is used for editing the property of the basic field in each property edit box 51. Then, as for the data source property, the eleventh operation is filled in the above formula in the data source property edit box 51. For example, in a case where the first target element generated by the first basic field 31a is, for example, the "Body mass index" element, the eleventh operation is to fill in the formula representing the above corresponding relationship in the data source property edit box 51.

In response to the eleventh operation, displaying the edited property in each property edit box 51 (S25), includes:

S251, in response to the eleventh operation, displaying a data source property representing the corresponding relationship in the data source property edit box 51 of the first basic field.

For example, as shown in FIG. 2C, in the properties menu 5 of the single line text box, the corresponding formula is entered in the data source property edit box 51 to set the content of the data source property of the single line text box.

The follow-up form management method further includes:

S7, as shown in FIG. 7, in response to an operation instruction for opening a follow-up task execution interface, displaying the follow-up task execution interface 700. The follow-up task execution interface 700 includes a follow-up form 100 included in a follow-up task created for a target patient. The follow-up form 100 includes a first target element and a second target element, both of which have an edit box.

For example, as shown in FIG. 7, in the follow-up form 100, the first target element 2 is the "Body mass index" element, and the second target elements 2 are the "Height" element and the "Weight" element. The first target element 2 and the second target elements each have an edit box 2a.

In response to the operation instruction for executing the follow-up task, executing the follow-up task (S8), includes S81 and S82. In S81, a thirteenth operation entered in the edit box of the second target element 2 is received, the thirteenth operation being used for entering target content in the edit box 2a of the second target element 2.

For example, the thirteenth operation is to enter the height and weight of the patient in the edit boxes 2a of the "Height" element and the "Weight" element, respectively.

In S82, in response to the thirteenth operation, the target content is displayed in the edit box of the second target element, and the content obtained according to the corresponding relationship represented by the data source property is automatically displayed in the edit box of the first target element.

When the properties of the basic field that generates the first target element are edited, the corresponding relationship between height, weight and body mass index is edited in the data source property edit box, and the content of the data source property is set in advance. In this way, during execution of the follow-up task, when the second user fills in the form 100, he only needs to enter the corresponding content in the edit boxes 2a of the "Height" element and the "Weight" element, and the content of the "Body mass index" element will be automatically determined and displayed in the edit box. Since there is no need for manual calculation, it may be possible to improve the efficiency and accuracy, and save time. For example, as shown in FIG. 1B, the current value of the "Height" property is 1.76, and the current value of the "Weight" property is 90, then the current value of the "Body mass index" property can be automatically determined as 28.9.

In some other embodiments, the plurality of fields include a third basic field; the third basic field is used for generating a third target element, and at least one property edit box of the third basic field includes a data source property edit box.

In response to the eleventh operation, displaying the edited property in each property edit box 51 (S25), includes S251'.

In S251', in response to the eleventh operation, the data source property linked with the background database is displayed in the data source property edit box 51 of the third basic field, the background database having stored therein content of the target element corresponding to the basic field 31*a*.

For example, the background database is, for example, a database of a hospital's electronic medical record system or a health management system. After the data source property of the basic field 31*a* is bound to the background database, when the second user fills in the element generated by the basic field 31*a*, the corresponding content may be automatically retrieved from the background database without manual filling, thus improving the efficiency and accuracy.

The follow-up form management method further includes S7.

In S7, as shown in FIG. 7, in response to an operation instruction for opening a follow-up task execution interface, the follow-up task execution interface 700 is displayed. The follow-up task execution interface 700 includes the follow-up form 100 included in the follow-up task created for the target patient. The follow-up form includes the third target element, and the third target element has an edit box.

For example, as shown in FIG. 7, in the follow-up form 100, the third target element 2 is a "Follow-up date" element, and the third target element has an edit box 2*a*.

In response to the operation instruction for executing the follow-up task, executing the follow-up task (S8), includes S81' and S82'. In S81', a fourteenth operation entered in the edit box 2*a* of the third target element is received, the fourteenth operation being used for selecting the edit box 2*a* of the third target element.

For example, the fourteenth operation is to select the edit box 2*a* of the "Follow-up date" element.

In S82', in response to the fourteenth operation, content in the background database linked with the data source property of the third target element is automatically displayed in the edit box of the third target element.

For example, considering an example where the third basic field 31*a* is date and time, the content of the title property in the properties menu is set to be "Follow-up date", then the third target element generated by the basic field 31*a* is the "Follow-up date" element. In the properties menu, the content of the data source property is set to be bound to the background database. For example, the background database stores the patient's initial visit time, the set follow-up interval and the current date and time therein. Then, according to the initial visit time and the set follow-up interval, and the current date and time, the specific content of the follow-up date may be obtained. For example, in FIG. 1B, the content of "Follow-up date" in the form 100 is automatically filled in as "Dec. 4, 2018 11:34:25", without needing the second user to fill in manually.

Alternatively, considering an example where the third basic field 31*a* is a single line text box, the content of the title property in the properties menu is set to be "Name", then the third target element generated by the basic field 31*a* is the "Name" element. In the properties menu, the content of the data source property is set to be bound to the background database. For example, the background database is the database of the medical data processing system. The database of the medical data processing system stores the patient's name, gender, age, height, weight and other information therein. When the second user fills in the form, the content of the "Name" element may be loaded directly without manual input.

In some embodiments, as shown in FIGS. 2B to 2D, in the field display area 3 of the scale making tool interface 200, the plurality of fields 31 include at least one commonly used field 31*b*, and the commonly used field 31*b* includes at least one edited property.

For example, as shown in FIG. 2D, the commonly used fields 31*b* include a "Follow-up manner" commonly used field 31*b*, a "Follow-up date" commonly used field 31*b*, a "Symptoms" commonly used field 31*b*, etc. Each commonly used field 31*b* includes at least one edited property. In an example where the commonly used field 31*b* is the "Follow-up manner" commonly used field 31*b*, the "Follow-up manner" commonly used field 31*b* includes a title property, a default prompt text property, an options property, a description property and a fill-in setting property. The content of the properties has been edited and saved. The commonly used field 31*b* may be directly used as a target element.

Figure 10B:
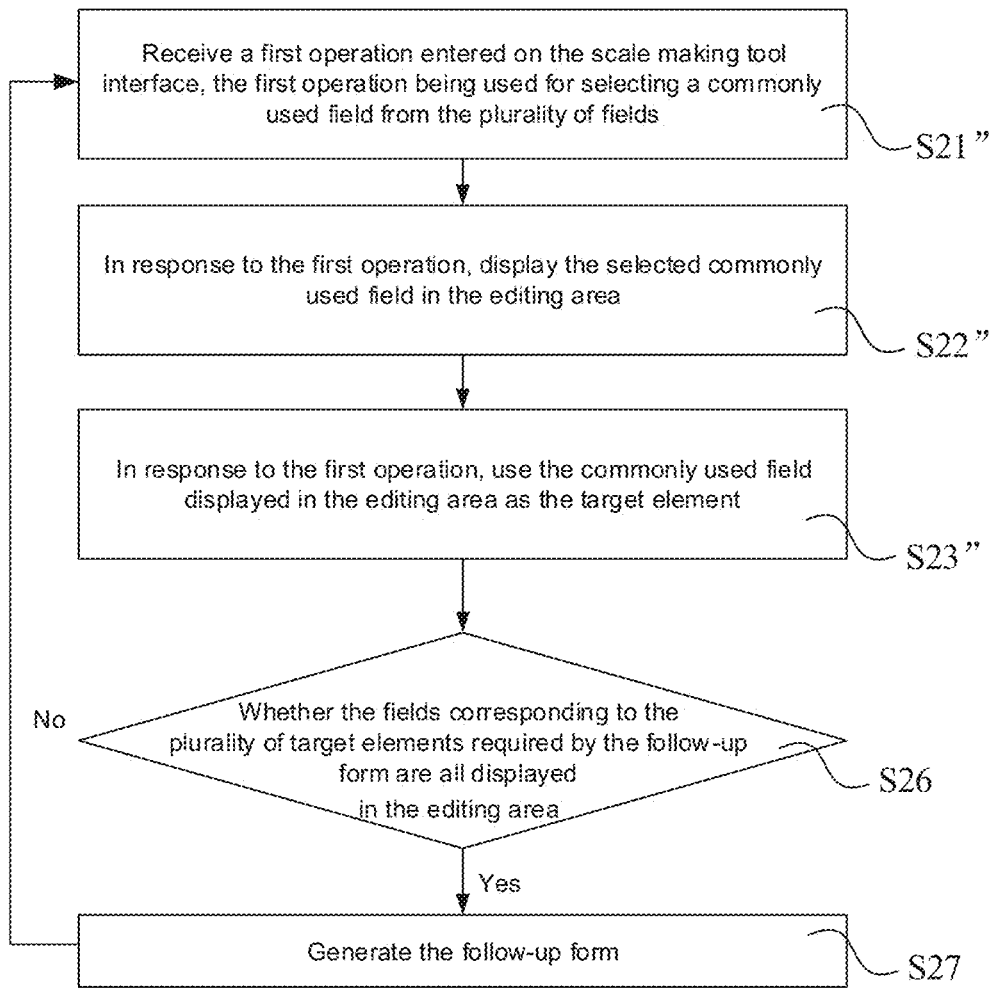
FIG. 10B is yet another flowchart of a follow-up form management method, according to some embodiments of the present disclosure.

As shown in FIG. 10B, in a case where the field 31 selected by the first operation is a commonly used field 31*b*, the above S21 is S21": receiving a first operation entered on the scale making tool interface 200, and the first operation being used for selecting a commonly used field 31*b* from the plurality of fields 31. The above S22 is S22": in response to the first operation, displaying the selected commonly used field 31*b* in the editing area 4. For example, as shown in FIG. 2D, the selected commonly used field 31*b* is the "Blood pressure" commonly used field 31*b*.

In the above case, after S22", the step of malting the follow-up form 100 in S2 further includes:

S23": in response to the first operation, using the commonly used field 31*b* displayed in the editing area 4 as the target element 2.

For example, the first operation is to select a commonly used field 31*b* and drag the commonly used field 31*b* to the target position of the editing area 4. In response to the first operation, the commonly used field 31*b* displayed in the editing area 4 is used as the target element 2. This is because the commonly used field 31*b* includes at least one edited property, so the commonly used field 31*b* may be directly used as the target element. For example, as shown in FIG. 2C, the "Blood pressure" common field 31*b* is set in the editing area 4 to generate the "Blood pressure" element.

In some embodiments, as shown in FIG. 2B, the plurality of fields 31 include a plurality of commonly used fields 31*b*, and the plurality of commonly used fields 31*b* include at least one common commonly used field and at least one private commonly used field.

The common commonly used field is able to be used as a target element in at least two types of follow-up forms to be made, and the private commonly used field is able to be used as a target element in one type of follow-up form to be made. That is to say, the common commonly used field may be used in at least two types of different follow-up forms, and the private commonly used field may only be used in one type of follow-up form to be made, and may not be used in other types of follow-up forms.

For example, considering the hypertensive patient follow-up service record form shown in FIG. 1A and the type 2 diabetic patient follow-up service record form shown in FIG. 10 as examples, the two types of follow-up forms 100 include a plurality of common target elements, such as the "Follow-up manner" target element and the "Follow-up date" target element. Each form 100 further includes its own typical elements, for example, the type 2 diabetic patient follow-up service record form shown in FIG. 10 further includes the typical "Heart rate" element and "Salt intake" element.

As shown in FIG. 7, the "Height" commonly used field, the "Weight" commonly used field, the "Follow-up manner" commonly used field, and the "Follow-up date" commonly used field are all common commonly used fields. The content of the edited property of the common field is universal, and may be used as the target element in at least two types of forms to be created; therefore, it may be used in different forms. For example, the "Follow-up manner" commonly used field may be used in the hypertensive patient follow-up service record form shown in FIG. 1A, and may also be used in the type 2 diabetic patient follow-up service record form shown in FIG. 1C.

For example, as shown in FIG. 7, the "Heart rate" commonly used field 31b is a private commonly used field. The "Heart rate" commonly used field may only be used in the type 2 diabetic patient follow-up service record form shown in FIG. 10, and may not be used in the hypertensive patient follow-up service record form shown in FIG. 1A.

The plurality of commonly used fields 31b are divided into at least one common commonly used field and at least one private commonly used field according to the scope of use, which facilitates the management of the plurality of commonly used fields 31b. It also helps the first user to quickly select a required commonly used field 31b from the corresponding common commonly used fields and the private commonly used fields when creating a form, so as to set the commonly used field 31b in the editing area 4 to generate the target element 2. This is conducive to the rapid production of forms and improves the efficiency.

Figure 11:
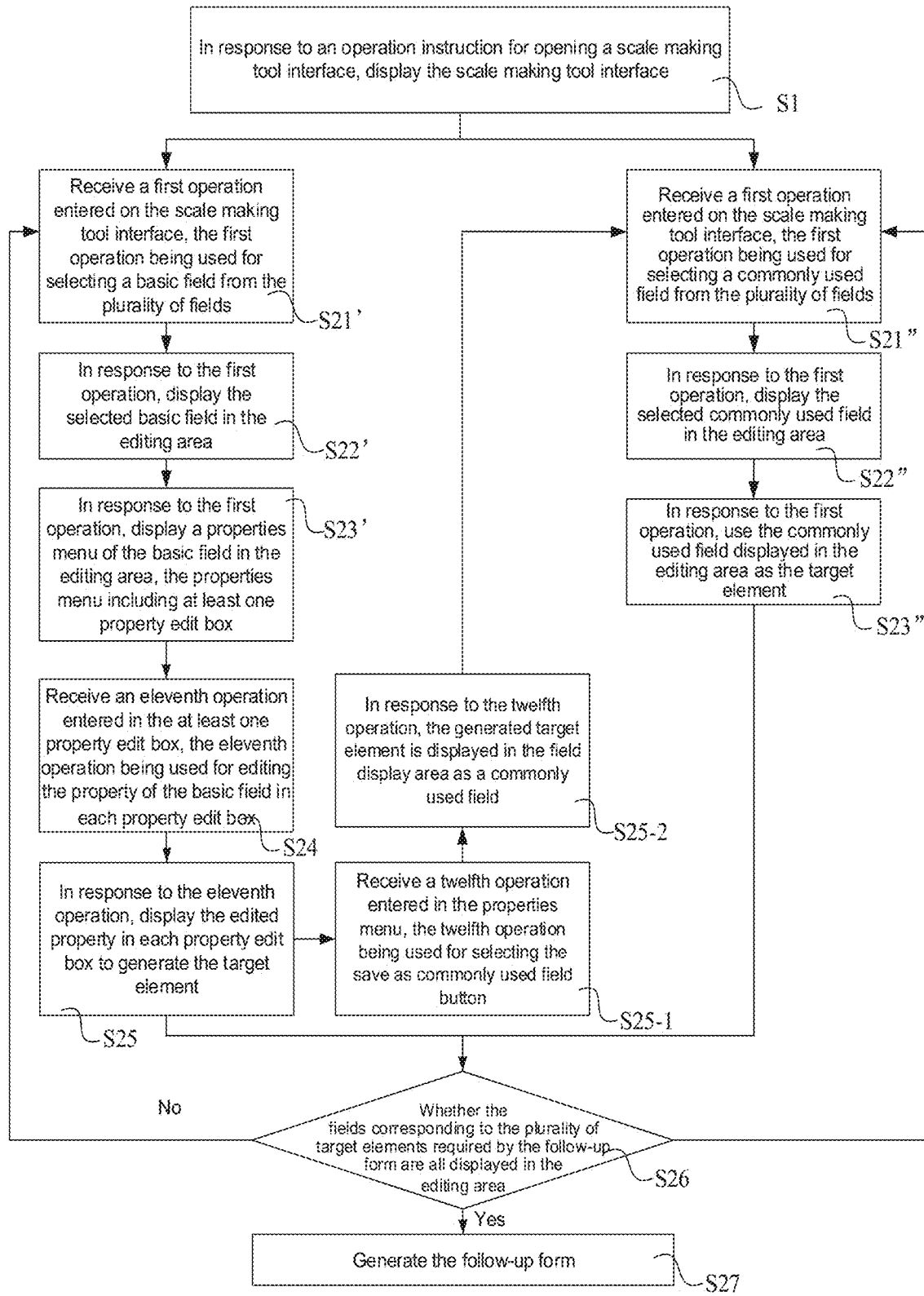
FIG. 11 is yet another flowchart of a follow-up form management method, according to some embodiments of the present disclosure.

In some embodiments, the method includes a method of generating target elements by using the basic field 31a and the commonly used field 31b simultaneously to generate a form. As shown in FIG. 11, and referring to FIGS. 2A to 2E, the method includes following steps.

In S1, in response to an operation instruction for opening the scale making tool interface, the scale making tool interface 200 is displayed. As shown in FIGS. 2A to 2G, the scale making tool interface 200 includes a field display area 3 and an editing area 4; the field display area 3 includes a plurality of fields 31, and the editing area 4 is used for making a follow-up form. The form to be made includes a plurality of target elements, and each target element is generated by a single field 31.

Generating the target element by using the basic field 31a includes the following S21' to S25.

In S21', as shown in FIGS. 2B and 20, a first operation entered on the scale making tool interface 200 is received, the first operation being used for selecting a basic field 31a from the plurality of fields 31.

For example, the first operation is to select a field 31 from the plurality of fields 31 and drag the field 31 to the target position in the editing area 4. The selected field 31 is, for example, a single line text box.

In S22', in response to the first operation, the selected basic field 31 is displayed in the editing area 4.

For example, as shown in FIG. 2C, the single line text box is displayed in the editing area 4.

In S23', in response to the first operation, a properties menu 5 of the basic field 31a is displayed in the editing area 4. The properties menu 5 includes at least one property edit box 51.

For example, as shown in FIG. 2C, in response to the first operation, the properties menu 5 of the single line text box is displayed in the editing area 4.

In S24, an eleventh operation of entered in the at least one property edit box 51 is received, the eleventh operation being used for editing the property of the basic field in each property edit box 51.

For example, as shown in FIG. 2C, the eleventh operation may be that the first user uses a mouse to click a property edit box 51 to select it, and uses a keyboard to enter corresponding content in the property edit box 51. For example, the title property, description property, default prompt text property, fill-in setting property and data source property in the properties menu 5 of the single line text box are edited. For details, reference may be made to the previous description, and details will not be repeated here.

In S25, in response to the eleventh operation, the edited property is displayed in each property edit box 51 to generate the target element.

For example, as shown in FIG. 2C, the edited property is displayed in each property edit box 51 and the single line text box is generated into a "Body mass index" element. At this time, the operation is caused to proceed to S26, and it is determined whether the fields 31 corresponding to the plurality of target elements required by the follow-up form are all set in editing area 4. If not, return to S21', and continue to perform operations from S21' to S25; if yes, proceed to S27 to generate the form.

Through the steps of S21' to S25, the corresponding target elements may be sequentially generated by the basic fields 31a. In this way, the purpose of using the basic fields 31a to generate the target elements to form part of the content of the follow-up form to be made may be realized.

Further, after the steps of S21' to S25 are completed each time, the generated target element may be saved as a commonly used field through S25-1 and S25-2, so as to be used next time.

In S25-1, a twelfth operation entered in the properties menu is received, the twelfth operation being used for selecting the save as commonly used field button.

For example, as shown in FIGS. 2B and 2C the properties menu 5 of the basic field 31a includes the save button and the save as commonly used field button, and the twelfth operation is an operation performed by the first user. For example, after generating the "Follow-up manner" target element by the basic field 31a in S25, the user clicks the save as commonly used field button to save the generated target element as a commonly used field 31b.

In S25-2, in response to the twelfth operation, the generated target element is displayed in the field display area 3 as a commonly used field 31b.

For example, as shown in FIGS. 2B and 20, the field display area 3 of the scale making tool interface 200 displays a commonly used field 31b of "Follow-up manner".

Through the above steps of S25-1 and S25-2, the target element generated by using the basic field 31a may be saved as a commonly used field 31b, In this way, when the form is made this time, the saved commonly used field 31b may be directly used to generate the target element in the following 321; alternatively, when a new form is created next time, the saved commonly used field 31*b* may be directly used, which facilitates the making of the form.

Generating the target element by using the commonly used field 31*b* includes the following S21" to S23".

In S21", a first operation entered on the scale making tool interface 200 is received, the first operation being used for selecting a commonly used field 31*b* from the plurality of fields 31. For example, the first operation is received, and the commonly used field 31*b* selected by the first operation is the "Follow-up manner" commonly used field 31*b*.

For example, the commonly used field 31*b* may also be a commonly used field 31*b* saved in the field display area 3 through the S33 and S34 after generating the target element by using the basic field 31*a* in the process of creating the form. For example, the "Follow-up manner" commonly used field 31*b* selected by the first operation is the "Follow-up manner" commonly used field 31*b* saved in the field display area 3 through S25-1 and S25-2.

In S22", in response to the first operation, the selected commonly used field 31*b* is displayed in the editing area 4.

As shown in FIGS. 2O and 2D, the "Follow-up manner" commonly used field 31*b* is displayed in the editing area 4.

In S23", in response to the first operation, the commonly used field 31*b* displayed in the editing area 4 is used as the target element 2.

For example, the "Follow-up manner" commonly used field 31*b* is used as the "Follow-up manner" element. At this time, the operation is caused to proceed to S26, and it is determined whether the plurality of target elements required by the follow-up form are all set in the editing area 4. If no, return to S21, and continue to perform the steps from S21" to S23"; if yes, proceed to S27 to generate a follow-up form.

Through the steps of S21" to S23" above, the corresponding target elements may be sequentially generated by the commonly used fields 31*b*, so that the commonly used fields 31*b* are used to generate target elements to form part of the content of the form to be created.

In the above embodiment, some of the plurality of target elements included in the follow-up form to be made may be generated through the commonly used fields 31*b*, and some other target elements may be generated through the basic fields 31*b*. After the target element is generated by using the basic field 31*b*, the target element may be saved as a commonly used field, so as to be used directly next time. The above S21' to S25 and S21" to S23" are in no particular order. According to the determination result of S26, S21' to S25 and S21" to S23" may be executed multiple times until the plurality of target elements required by the form are all set in the editing area 4.

For example, the form to be created is the hypertensive patient follow-up service record form shown in FIG. 1A, and the target elements included in the form are the "Follow-up date" element, the "Follow-up manner" element, the "Symptoms" element, the "Body mass index" element, etc. In the process of creating the form 100, the first user first checks whether there is a corresponding commonly used field 31*b* in the commonly used fields 31*b* in the field display area 3. For example, as shown in FIGS. 2B to 2D, the commonly used fields 31*b* include the "Follow-up date" commonly used field 31*b*, the "Follow-up manner" commonly used field 31*b* and the "Symptoms" commonly used field 31*b*. Then, the above commonly used fields 31*b* may be set in the editing area 4 in sequence through S21" to S23", so as to generate the corresponding target elements. For the "Body mass index" element, a single line text box may be selected from the plurality of basic fields 31*a*, and steps S21' to S25 are performed to generate the "Body mass index" element from the single line text box and set it in the editing area 4. When creating a form, the first user may choose freely according to the target elements 2 required by the form and the types of fields 31 included in the field display area, which is highly flexible.

Through the above method, by using both the basic field 31*a* and the commonly used field 31*b* to generate the target element 2, the creation of the form may be quickly completed according to the needs of the first user, the time of creating the form may be shortened, and the work efficiency of the first user may be improved. Moreover, there is no need to adjust the internal program when creating different forms, which reduces the maintenance cost.

Figure 2F:
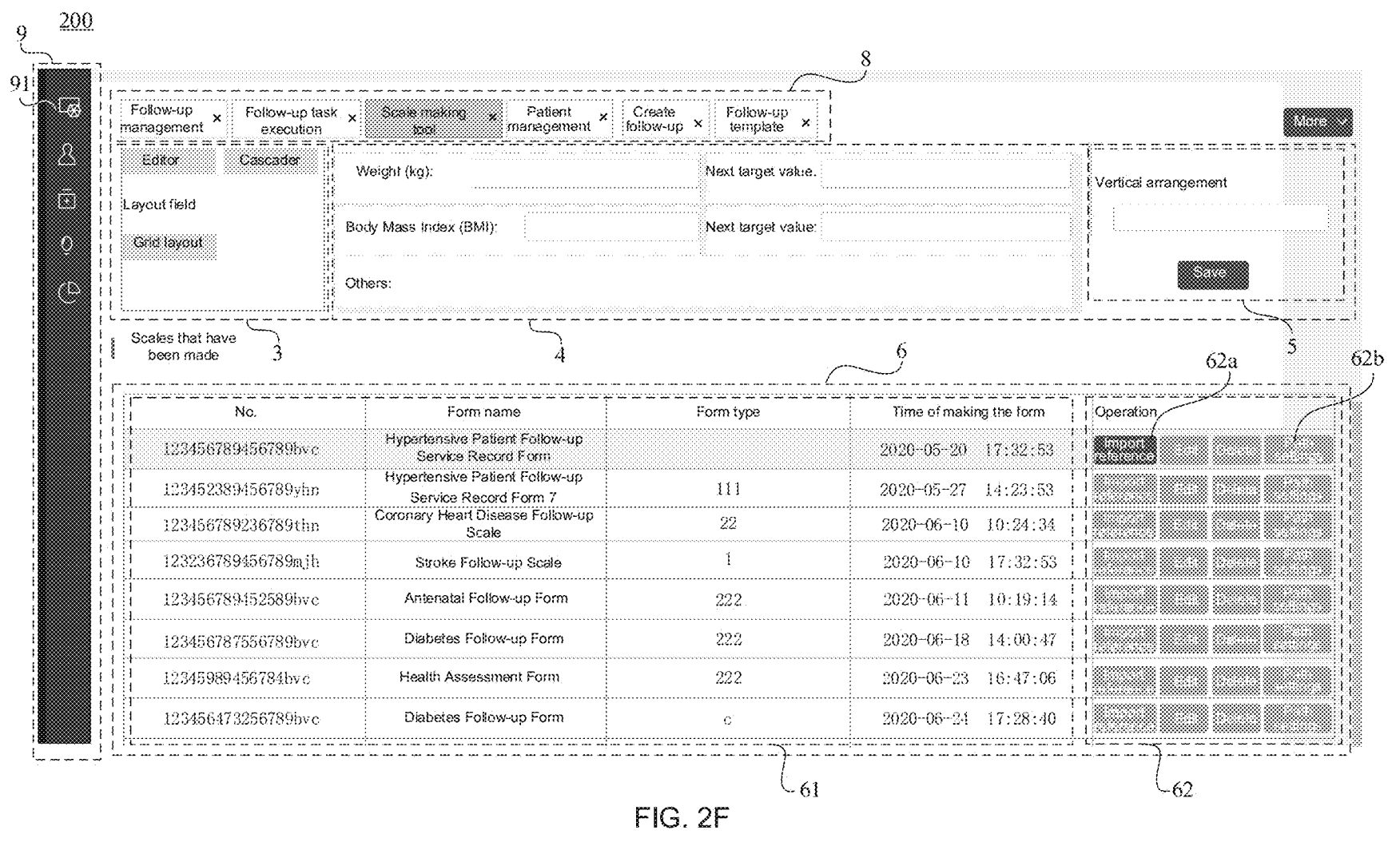

In some embodiments, the scale making interface 200 further includes a form area 6 (as shown in FIGS. 2E to 2F) and a submission bar 7 (as shown in FIGS. 2B to 2D). The pages shown in FIGS. 2D to 2F are each the scale making tool interface 200, and the page shown in FIG. 2E or FIG. 2F may be selected to be displayed through the scroll bar on the right. As shown in FIG. 2D, the submission bar 7 includes a view button, a clear button, a preview button and a generate form button. The view button is used for viewing the content of the elements in the editing area 4; the clear button is used for deleting all the elements set in the editing area 4; the preview button is used for previewing the generated form, and the generate form button is used for submitting and saving the generated form. As shown in FIG. 2E, the form area 6 includes a plurality of forms that have been generated, and the form area is used for displaying the names of the generated forms.

The step of making the form in S2 further includes S28 and S29 of submitting and saving the completed follow-up form 100.

In S28, a fifteenth operation entered in the submission bar 7 is received, the fifteenth operation being used for selecting the generate form button to submit and save the generated follow-up form.

For example, after the form 100 is made, the first user clicks the generate form button in the submission bar 7 to submit and save the generated follow-up form.

In S29, in response to the fifteenth operation, the generated follow-up form is saved, and the name of the saved follow-up form is displayed in the form area.

In response to the fifteenth operation, the generated form saved in the form area. For example, the generated follow-up form is the hypertensive patient follow-up service record form shown in FIG. 1A and the follow-up form is saved; the form area shows that the name of the saved follow-up form is "Hypertensive Patient Follow-up Service Record Form".

As a possible design, the step of making the follow-up form in 52 further includes S27-1 and S27-2 of previewing the created form 100 before S28.

In S27-1, a sixteenth operation entered in the submission bar 7 is received, the sixteenth operation being used for selecting a preview button to preview the generated follow-up form.

For example, after the form 100 is created, the first user clicks the preview button in the submission bar 7 to preview the generated form.

In S27-2, in response to the sixteenth operation, the generated follow-up form is displayed in the editing area 4.

By displaying the generated form in the editing area 4, it may be possible to view the form style and determine whether the generated follow-up form is consistent with the follow-up form to be created. If it is not consistent, the position, format, content, etc. of each element in the generated follow-up form may be modified in the editing area 4 until satisfactory results are obtained.

In some embodiments, as shown in FIG. 2D, the field display area 3 further includes a layout field, for example, a grid layout field 31*d*. After S27-2, the method further includes a step of adjusting the position and format of each element in the follow-up form, and this step includes: in response to an operation of selecting at least two target elements 2 in the editing area 4, and in response to an operation of selecting a grid layout field 31*d*, displaying a grid layout menu 5' in the editing area 4, the grid layout menu 5' including a plurality of layout edit boxes; in response to an operation of editing the plurality of layout edit boxes, displaying the edited content in the plurality of layout edit boxes, and adjusting positions of the selected at least two target elements 2 according to the edited content.

For example, as shown in FIG. 2D, the operation of the first user to select at least two target elements 2 in the editing area 4 is to use the mouse and the Ctrl key to select the follow-up date target element and the follow-up manner target element. Then, the first user selects the grid layout field 31*d*, so that the grid layout menu 5' is displayed in the editing area 4. The grid layout menu 5' includes a plurality of layout edit boxes, such as a grid interval edit box, a column configuration item edit box, etc. By editing the plurality of layout edit boxes, the position, interval, layout, etc, of the selected target elements 2 may be adjusted, so that the layout of the follow-up form achieves the desired effect.

In some embodiments, the sixteenth operation is further used for selecting a preview effect of the form, and the preview effect includes a paper effect and an effect displayed on a screen of a mobile terminal.

In response to the sixteenth operation, displaying the generated form in the editing area 4 (S27-2) includes: in response to the sixteenth operation, displaying the generated form in the editing area 4 with the paper effect or with the effect displayed on the screen of the mobile terminal.

Figure 12:
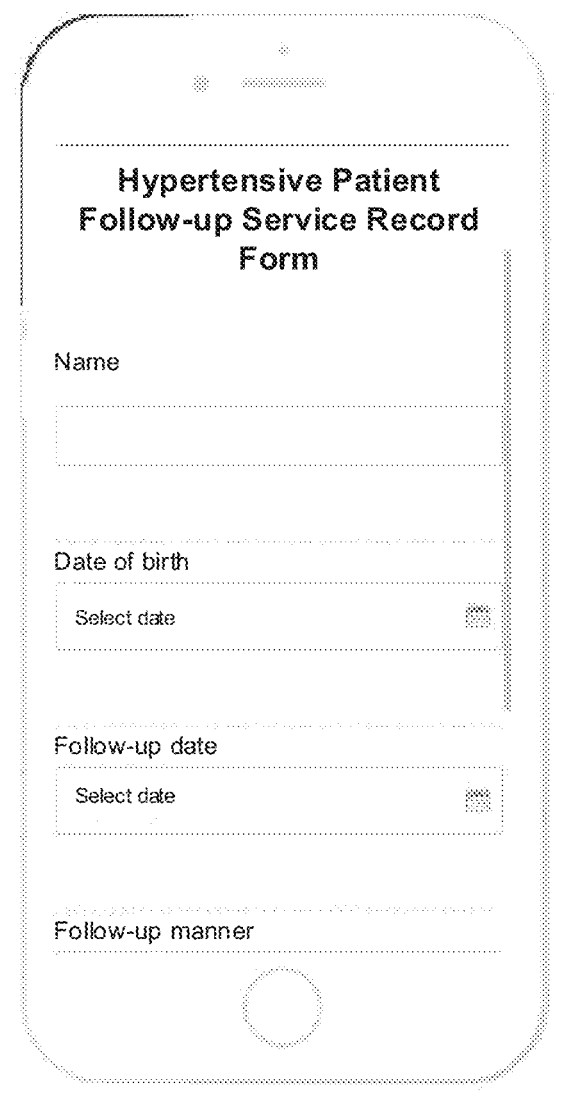

The paper effect, for example, refers to the effect of the entire form in A4 paper size or other paper sizes displayed on the computer screen. For example, the effect of the form shown in FIGS. 1A to 1C is the paper effect. The effect displayed on the screen of the mobile terminal, for example, refers to the effect of the form displayed on the screen of the mobile phone. For example, the effect of the form shown in FIG. 12 is the effect displayed on the screen of the mobile terminal.

In a case where the generated form is displayed in the editing area 4 with the effect displayed on the screen of the mobile terminal, due to the small screen of the mobile phone, all the elements included in the generated form cannot be displayed on one page. The elements may be displayed in sequence according to the sequence numbers generated by default when the elements are inserted; alternatively, specific sequence numbers may be assigned to the elements, and the elements may be displayed in sequence according to the assigned sequence numbers.

In some embodiments, as shown in FIG. 2E, the form area 6 includes a list sub-area 61 and an operation sub-area 62. The list sub-area 61 includes a name of at least one saved follow-up form, and the saved follow-up form includes a plurality of set elements. The operation sub-area 62 includes at least one import reference option 62*a*, and each saved follow-up form corresponds to a single import reference option 62*a*. The set element refers to an element whose properties are all set.

For example, the form to be created is the type 2 diabetic patient follow-up service record form shown in FIG. 1C the step of making the follow-up form in S2 further includes S29-1 and S29-2.

In S29-1, a seventeenth operation entered in an operation sub-area 62 is received, the seventeenth operation being used for selecting an import reference option.

For example, the seventeenth operation is to click the mouse to select the import reference option 62*a* corresponding to the first form "Hypertensive Patient Follow-up Service Record Form" in the operation sub-area 62.

In S29-2, in response to the seventeenth operation, the saved follow-up form corresponding to the selected import reference option is displayed in the editing area 4, and the follow-up form used as the basic form.

In response to the seventeenth operation, the "Hypertensive Patient Follow-up Service Record Form" is displayed in the editing area 4, and the "Hypertensive Patient Follow-up Service Record Form" is used as a basic form. For example, the follow-up forms shown in FIGS. 1A and 1B are the "Hypertensive Patient Follow-up Service Record Form".

In S29-3, an eighteenth operation entered on the scale making tool interface 200 is received, the eighteenth operation being used for modifying at least one set element among the plurality of set elements in the basic form. The at least one set element is inconsistent with the target elements of the follow-up form to be made.

For example, in the "Hypertensive Patient Follow-up Service Record Form" (a basic form) shown in FIGS. 1A and 1B, and the "Type 2 Diabetic Patient Follow-up Service Record Form" (a form to be created) shown in FIG. 10, both the "Follow-up date" element and the "Follow-up manner" element of the two are the same, but the "Symptoms" element of the two are not the same. For example, the properties of the "Symptoms" element include a title property, a description property, an options property and a data source property. In both forms, the content of the title property is "Symptoms". However, in the "Hypertensive Patient Follow-up Service Record Form", the options property of the "Symptoms" element includes "Asymptomatic", "Headache and dizziness", "Nausea and vomiting", etc.; in the "Type 2 Diabetic Patient Follow-up Service Record Form", the options property of the "Symptoms" element includes "Asymptomatic", "Excessive thirst", "Excessive eating", etc. Therefore, at least one set element among the plurality of set elements in the basic form needs to be modified through the eighteenth operation. For example, the options property of the "Symptoms" element needs to be modified.

In S29-4, in response to the eighteenth operation, the at least one set element that is modified is set to generate the target element.

For example, in response to the eighteenth operation, the "Symptoms" element in the "Hypertensive Patient Follow-up Service Record Form" is modified to the "Symptoms" element in the "Type 2 Diabetic Patient Follow-up Service Record Form".

In S29-5, the step that the eighteenth operation is received and responded to repeatedly, until the plurality of set elements of the basic form are consistent with the plurality of target elements of the follow-up form to be made, so as to generate a new follow-up form.

Through the above steps, the saved follow-up form may be used as the basic form. If the content of the basic form is similar to that of the follow-up form to be made, by modifying the elements in the basic form that are inconsistent with those of the follow-up form to be made, it may be possible to quickly obtain a new follow-up form without needing to make a new form by sequentially setting the basic fields 31a and commonly used fields 31b to generate the target elements in sequence. As such, the form making efficiency is improved, and the user's time is saved.

In some embodiments, the step of making the follow-up form in S2 further includes: after the selected field 31 is displayed in the editing area 4 and the target element is generated by the field 31 in response to the first operation, numbering the generated target element, different target elements being numbered differently.

Figure 2G:
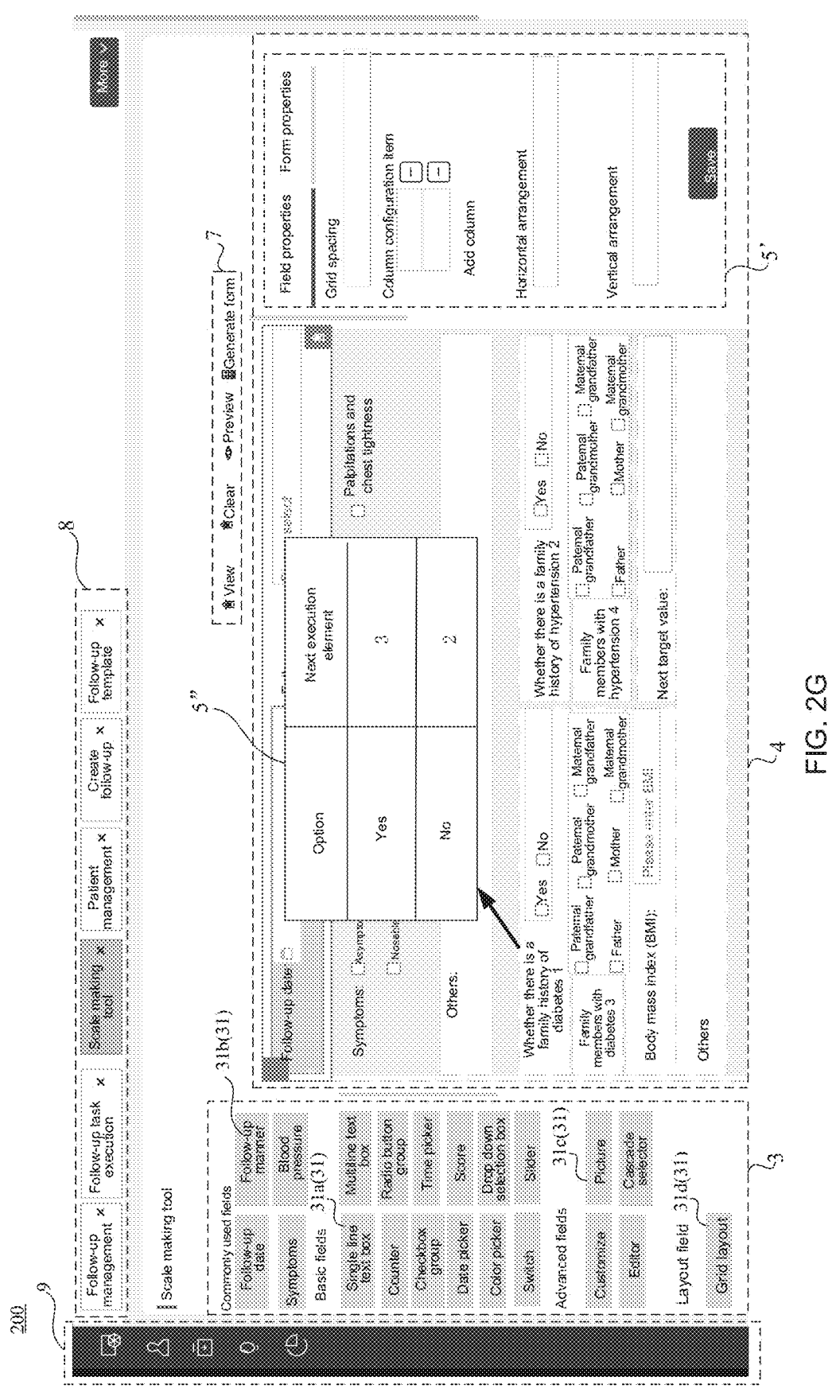

For example, as shown in FIG. 2G, the target elements in the follow-up form 100 to be made include the "Whether there is a family history of hypertension" element, the "Whether there is a family history of diabetes" element, the "Family members with diabetes" element, and the "Family members with hypertension" element. The "Whether there is a family history of hypertension" element and the "Whether there is a family history of diabetes" element both have two options, namely, "Yes" and "No". The "Family members with diabetes" element and the "Family members with hypertension" element both have six options, namely, a "Paternal grandfather" option, a "Paternal grandmother" option, a "Maternal grandfather" option, a "Maternal grandmother" option, a "Father" option and a "Mother" option.

The above four elements are numbered. For example, the "Whether there is a family history of hypertension" element, the "Whether there is a family history of diabetes" element, the "Family members with diabetes" element, and the "Family members with hypertension" element are numbered 2, 1, 3, and 4, respectively.

As shown in FIG. 2F, the form area 6 includes a list sub-area 61 and an operation sub-area 62. The list sub-area 61 includes at least one saved follow-up form, and the saved follow-up form includes a plurality of set elements. The operation sub-area 62 includes at least one path settings option 62b, and each of the saved follow-up forms corresponds to a single path settings option 62b.

The step of making the follow-up form in S2 further includes the following steps.

In S29-1', a nineteenth operation entered on the scale making tool interface 200 is received, the nineteenth operation being used for selecting a single path settings option 62b in the operation sub-area 62.

For example, the nineteenth operation is to select the path settings option 62b corresponding to the first follow-up form in the operation sub-area 62.

In S29-2', in response to the nineteenth operation, in the editing area 4, the saved follow-up form corresponding to the selected path settings option is displayed, and numbers of a plurality of set elements in the follow-up form are displayed; the plurality of set elements including a first element and a plurality of second elements, and the first element having at least two options.

As shown in FIG. 2G, the first element is the "Whether there is a family history of diabetes" element, the second elements are the "Whether there is a family history of hypertension" element and the "Family members with diabetes" element. The numbers of the above three elements are 1, 2, and 3, respectively. The first element has at least two options, respectively, a "Yes" option and a "No" option.

In S29-21', a twentieth operation entered on the scale making tool interface 200 is received, the twentieth operation being used for selecting the first element.

For example, the twentieth operation is to double-click the "Whether there is a family history of diabetes" element with the mouse.

In S29-3', in response to the twentieth operation, an execution path menu of the first element is displayed, the execution path menu including an option item and a next execution element item, the option item including at least two option boxes of the first element, the next execution element item including at least two path edit boxes, and a edit box corresponding to an option box.

As shown in FIG. 2G, in response to the twentieth operation, an execution path menu 5" is displayed in the editing area 4, and the execution path menu 5" includes an "Option" item and a "Next execution element" item. The first element has at least two options, respectively, a "Yes" option and a "No" option. Therefore, the "Option" item includes two option boxes, respectively, a "Yes" option box and a "No" option box. Each option box corresponds to a path edit box. At this time, the path editing box is empty.

In S29-4', a twenty-first operation entered in the at least two path edit boxes is received, the twenty-first operation being used for editing a number of a next execution element of the first element under different options in each path editing box.

For example, as shown in FIG. 2G, with regard to the "Yes" option box, the path edit box is edited as 3; with regard to the "No" option box, the path edit box is edited as 2. That is, if the selection result of the "Whether there is a family history of diabetes" element is "Yes", then the "Family members with diabetes" element is executed; if the selection result of the "Whether there is a family history of hypertension" element is "No", then the "Family members with hypertension" element is executed.

In S29-5', in response to the twenty-first operation, the edited number is displayed in each path edit box.

Through S29-1' to S29-5', the setting of the element path between the first element and the second elements is realized, so that during execution of the follow-up task, when the second user fills in the follow-up form 100, if the "Yes" option of the first element is selected, it will automatically jump to a second element of the second elements, so that the second element is filled in next; if the "No" option of the first element is selected, it will automatically jump to another second element of the second elements, so that the another second element is filled in next. In this way, there is no need to manually determine the corresponding option and which element is the next execution element, which saves the time for determination and makes it quicker and more convenient to complete the follow-up form.

In some embodiments, considering a hospital as an example, different departments or sections in an institution use different follow-up forms, and even different personnel use different forms. To avoid confusion, the follow-up form management method further includes: after the follow-up form is made, authorizing access to the follow-up form. Authorization may be performed according to departments or personnel. After authorization, the follow-up form is published. When using the follow-up form, for example, when creating a follow-up task, different personnel may see the corresponding follow-up form. For example, doctors in charge of chronic diseases such as hypertension and diabetes may see the corresponding follow-up forms.

Step of S5, in response to the operation instruction for creating a follow-up task, creating a follow-up task including a follow-up form in the follow-up creation interface 400, will be described below.

It will be noted that the follow-up task includes follow-up time and follow-up content, that is, what kind of follow-up was done to the patient on which day. The follow-up content may be represented by a corresponding follow-up form 100.

It will be understood that the follow-up task includes the follow-up time and the follow-up form. For example, the follow-up time of a follow-up task is 2020-9-10, and the follow-up form is "Quality of Life Scale for Hypertensive Patients"; then, this follow-up task was to visit a hypertensive patient on Sep. 10, 2020 and record his quality of life.

In some embodiments, as shown in FIGS. 4A and 4B, the follow-up creation interface 400 includes a standard template area 10, and the standard template area 10 includes a template classification selection box 101. The template classification selection box 101 has a chronic disease options menu 101a. The chronic disease options menu 101a includes a plurality of chronic disease options A; each chronic disease option A corresponds to a follow-up template, and each follow-up template includes a plurality of follow-up forms and an interval time corresponding to each follow-up form. The interval time is the interval time between the current date when the follow-up task is created and the target return visit date.

Each chronic disease option may correspond to only one chronic disease. For example, the chronic disease option of hypertension corresponds to only one chronic disease of hypertension. Alternatively, each chronic disease option may correspond to at least two chronic diseases. For example, the chronic disease options of stage 1 hypertension correspond to two chronic diseases—hypertension and diabetes.

In response to the operation instruction for creating the follow-up task, creating the follow-up task including the follow-up form (S5), includes the following steps.

In S51, a second operation entered in the standard template area 10 is received, the second operation being used for selecting the template classification selection box 101.

In S52, in response to the second operation, the chronic disease options menu 101a including the plurality of chronic disease options A is displayed in the standard template area 10.

The second operation is that the user clicks the template classification selection box 101, so that a chronic disease options menu 101a including a plurality of chronic disease options A pops up in the template classification selection box 101.

In S53, a third operation entered in the standard template area 10 is received, the third operation being used for selecting a chronic disease option A from the plurality of chronic disease options A.

As shown in FIG. 4A, the corresponding chronic disease option A is selected according to the chronic disease of the target patient. For example, if the chronic disease of the patient is hypertension and diabetes, then the chronic disease option A of stage 1 hypertension should be selected.

In S54, in response to the third operation, a plurality of follow-up tasks are created in the standard template area, each follow-up task including a follow-up form and a corresponding return visit time. The follow-up form is a follow-up form in the follow-up template corresponding to the selected chronic disease option, and the return visit time is obtained according to a date of creating the follow-up task and the interval time corresponding to the follow-up form.

Figure 5A:
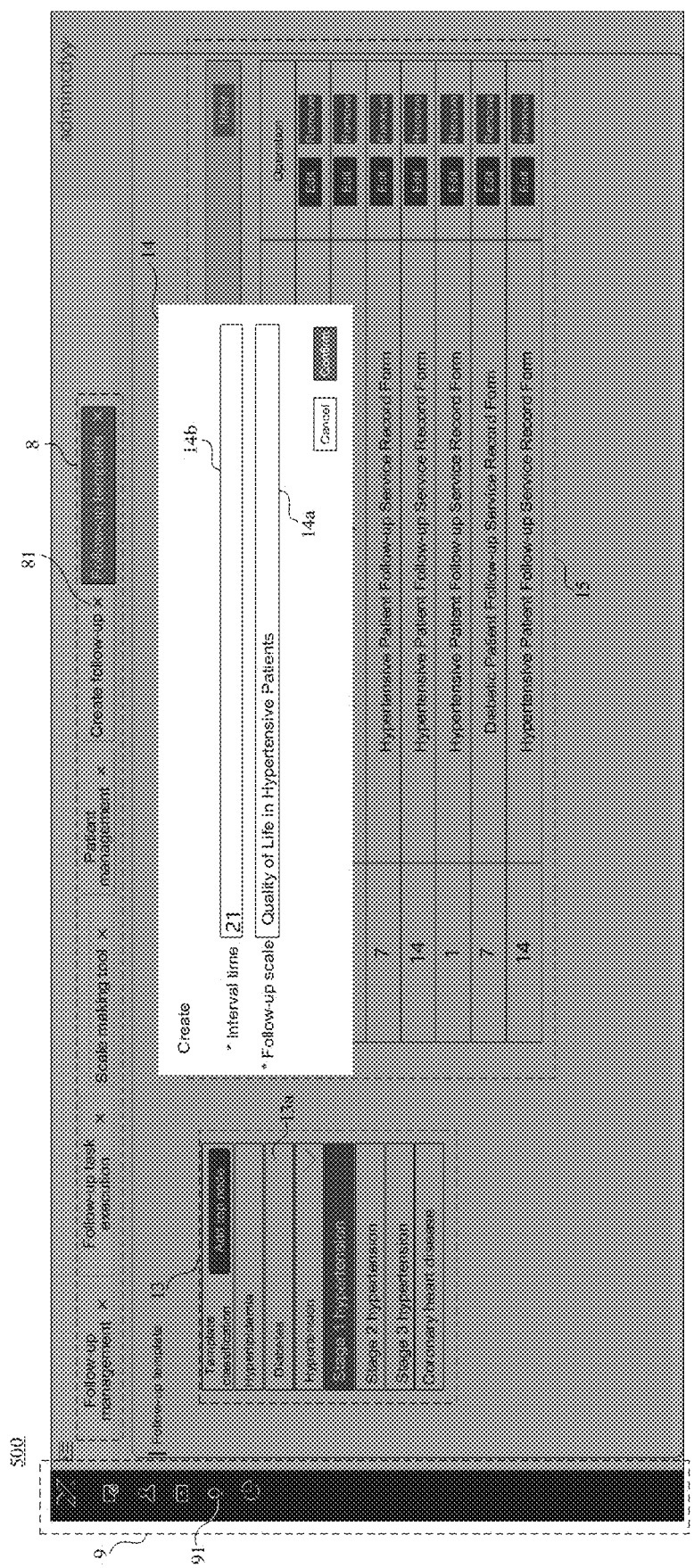
FIG. 5A is a schematic diagram of a follow-up template interface in a follow-up form management method, according to some embodiments of the present disclosure.
Figure 5B:
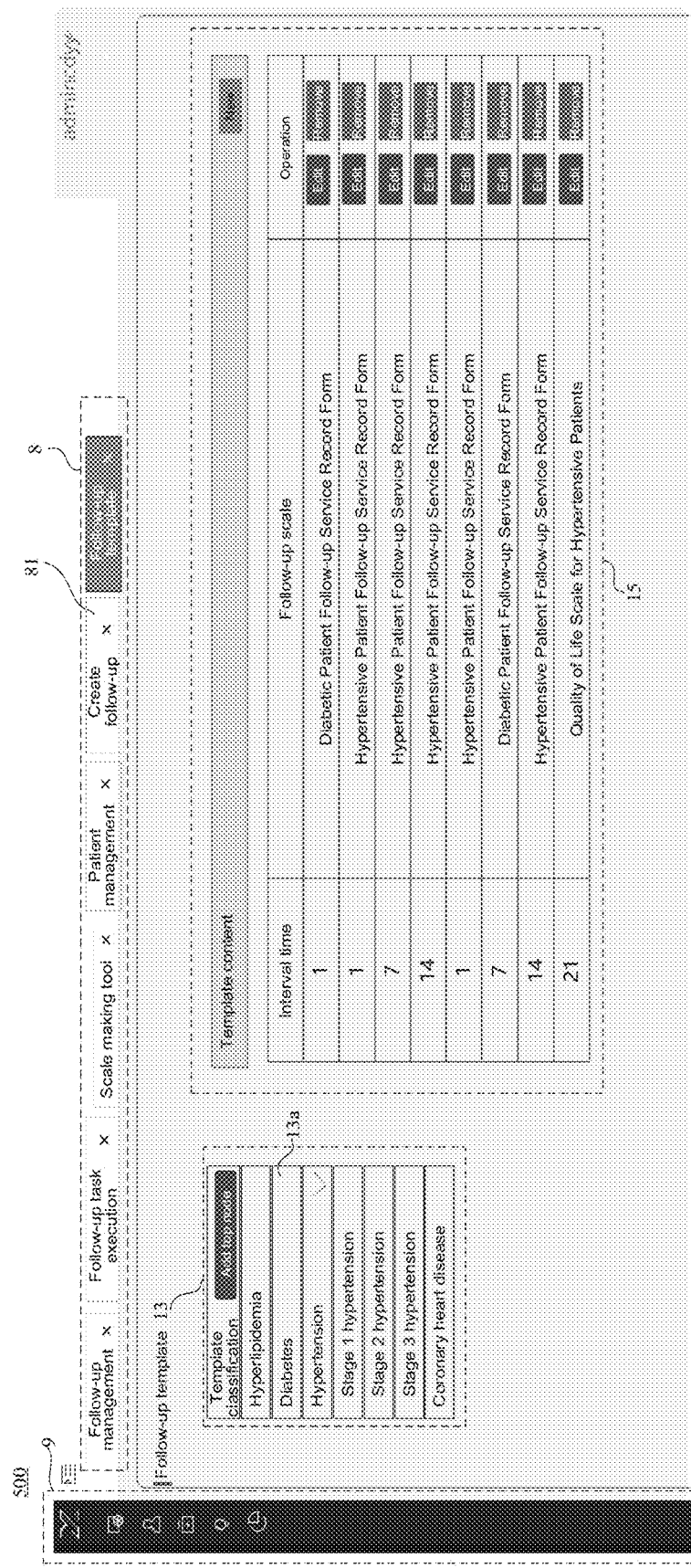
FIG. 5B is another schematic diagram of a follow-up template interface in a follow-up form management method, according to some embodiments of the present disclosure.

For example, FIG. 5B shows a follow-up template interface 500. The follow-up template in the follow-up template interface 500 is, for example, a follow-up template corresponding to the chronic disease option of stage 1 hypertension, and the follow-up template includes a plurality of follow-up forms and interval times corresponding to the follow-up forms. For example, the interval time corresponding to one of the hypertensive patient follow-up service record forms is 1, and the interval time corresponding to the quality of life scale for hypertensive patients is 21.

In response to the third operation, a plurality of follow-up tasks are created in the standard template area 10. Each follow-up task includes a follow-up form and a corresponding return visit time. The follow-up form is a follow-up form in the follow-up template corresponding to the selected chronic disease option of stage 1 hypertension. The return visit time is obtained according to the date of creating the follow-up task and the interval time corresponding to the follow-up form. As shown in FIG. 4B, considering an example where the date of creating the follow-up task is Jul. 13, 2020, according to the plurality of follow-up forms included in the follow-up template in FIG. 5B and the interval time corresponding to each follow-up form, the return visit time corresponding to each follow-up form may be obtained. For example, in the follow-up template, the interval times corresponding to two hypertensive patient follow-up service record forms are both 1, and the interval time corresponding to a diabetic patient follow-up service record form is 1. Then, in the plurality of follow-up tasks displayed in the standard template area 10, the first three tasks are: the follow-up form is a hypertensive patient follow-up service record form, and the corresponding return visit time is Jul. 14, 2020; the follow-up form is a diabetic patient follow-up service record form, and the corresponding return visit time is Jul. 14, 2020; and the follow-up form is a hypertensive patient follow-up service record form, and the corresponding return visit time is Jul. 14, 2020. Other tasks are analogous and details will not be repeated here.

In some embodiments, as shown in FIG. 8, the follow-up form management method further includes a step S9 of creating a follow-up template. S9 includes S91 and S92.

In S91, as shown in FIGS. 5A and 5B, in response to an operation instruction for opening a follow-up template interface, the follow-up template interface 500 is displayed. The follow-up template interface includes a template classification bar 13, and the template classification bar 13 includes a plurality of chronic disease options 13a.

The above operation instruction for opening the follow-up template interface is, for example, to select an icon 91, in the main menu bar 9, corresponding to the follow-up template interface 500.

In S92, in response to an operation instruction for creating a follow-up template, a follow-up template is created; the follow-up template including the plurality of follow-up forms and the interval time corresponding to each follow-up form. The follow-up form is the follow-up form corresponding to the chronic disease option selected from the plurality of chronic disease options under the operation instruction for creating the follow-up template, and the interval time is the interval time between a return visit data set for the selected chronic disease option and the date of creating the follow-up task.

In some embodiments, as shown in FIGS. 5A and 5B, the follow-up template interface 500 further includes a template content bar 15. The template content bar 15 includes a new button, and the template content bar 15 is used for displaying the created follow-up template.

In response to the operation instruction for creating the follow-up template, creating the follow-up template (S92), includes the following steps.

In S921, a fourth operation entered in the template classification bar 15 is received, the fourth operation being used for selecting a chronic disease option from the plurality of chronic disease options and for selecting the new button.

For example, if the follow-up template to be created is a follow-up template for a patient suffering from both hypertension and diabetes, the fourth operation is to select the "Stage 1 Hypertension Chronic Disease" option.

In S922, in response to the fourth operation, a follow-up template creation dialog box 14 is displayed on the follow-up template interface 500. The follow-up template creation dialog box 14 includes a follow-up form edit box 14a and an interval time edit box 14b as well as a confirm button and a cancel button. The follow-up form edit box 14a has at least one form option related to the selected chronic disease option, and each form option corresponds to a generated follow-up form.

For example, the fourth operation is to select the stage 1 hypertension chronic disease option, and the follow-up form edit box 14a has at least one form option related to the selected stage 1 hypertension chronic disease option. Each form option corresponds to a generated follow-up form, and the follow-up form may be, for example, a "Quality of Life Scale for Hypertensive Patients", a "Quality of Life Scale for Diabetic Patients", etc.

In S923, a fifth operation entered in the follow-up form edit box is received, the fifth operation being used for selecting a form option from the at least one form option.

For example, the fifth operation is to select an option corresponding to the "Quality of Life Scale for Hypertensive Patients" from the at least one form option.

In S924, in response to the fifth operation, a name of the follow-up form corresponding to the selected form option is displayed in the follow-up form edit box.

As shown in FIG. 5A, the name "Quality of Life Scale for Hypertensive Patients" of the follow-up form corresponding to the selected form option is displayed in the follow-up form edit box 14a.

In S925, a sixth operation entered in the interval time edit box 14b is received, the sixth operation being used for setting the interval time corresponding to the selected chronic disease option.

In S926, in response to the sixth operation, the set interval time is displayed in the interval time edit box 14b.

For example, as shown in FIG. 5A, the set interval time is displayed as 21 days in the interval time edit box 14b.

In S927, a seventh operation entered in the follow-up template creation dialog box is received, the seventh operation being used for selecting the confirm button.

In S928, in response to the seventh operation, the follow-up template is displayed in the template content bar.

As shown in FIG. 5B, in the last bar of the template content area 15, a record of the created follow-up template is displayed. That is, the interval time is 21 days, and the follow-up scale is the record of the "Quality of Life Scale for Hypertensive Patients". A plurality of records constitute a follow-up template corresponding to the chronic disease option of stage 1 hypertension.

In this way, when the plurality of follow-up tasks are created in the standard template area in response to the third operation in S54, the pre-created follow-up template may be called directly. When the user selects a chronic disease option A from the chronic disease options menu 101a in the standard template area 10, a corresponding follow-up task may be generated according to the pre-created follow-up template.

In some embodiments, as shown in FIGS. 4A and 4B, the follow-up creation interface 400 includes a custom area 11. The custom area 11 includes at least one custom item 111, and each custom item 111 includes a return visit content selection box 111a. The return-visit content selection box 111a has a form option menu 111a1 and the form option menu 111a1 includes a plurality of form options B. Each form option B corresponds to a generated follow-up form 100.

In response to the operation instruction for creating the follow-up task, creating the follow-up task including the follow-up form (S5), includes the following steps.

In S51', an eighth operation entered in the custom area 11 is received, the eighth operation being used for selecting a return visit content selection box 111a of a customized item 111.

For example, as shown in FIG. 4B, the eighth operation is to select the return visit content selection box 111a of the bottommost custom option 111.

In S52', in response to the eighth operation, a form options menu 111a1 including a plurality of form options B is displayed in the custom area 11.

As shown in FIG. 4B, in response to the eighth operation, a form option menu 111a1 including a plurality of form options B pops up on a side of the selected return visit content selection box 111a.

In S53', a ninth operation entered in the custom area 11 is received, the ninth operation being used for selecting a form option B from the plurality of form options B.

For example, as shown in FIG. 4B, the ninth operation is to select the form option B corresponding to the "Hypertensive Patient Follow-up Service Record Form" in the return visit content selection box 111a.

In S54', in response to the ninth operation, the follow-up task is created in the custom area 11, the follow-up task includes the follow-up form corresponding to the selected form option.

For example, as shown in FIG. 4B, the name "Hypertensive Patient Follow-up Service Record Form" is displayed in the selected return visit content selection box 111a, which indicates that the follow-up content of the created follow-up task is to follow up on hypertensive patients and keep records.

In some embodiments, in addition to the follow-up task, the follow-up task created in the custom area 11 further includes a return visit date.

As shown in FIGS. 4A and 4B, the custom item 111 includes a return visit date sub-item 111b.

As shown in FIG. 4B, in the first four custom items 111, the return visit date sub-item 111b has a fixed return visit date, and the return visit dates are one day later, one month later, two months later, and three months later, respectively. According to the current date when the follow-up task was created, the date corresponding to each return visit date sub-item 111b may be automatically determined and displayed. For example, if the current date of creating the follow-up task is Jul. 13, 2020, then in the first custom item 111, the return visit date of the return visit date sub-item 111b is Jul. 14, 2020, and the return visit dates of the return visit date sub-item 111b of the second custom item 111 to the fourth custom item 111 are Aug. 14, 2020, Sep. 14, 2020, and Oct. 14, 2020, respectively.

Alternatively, as shown in FIGS. 4A and 4B, in the fifth custom item 111, the return visit date sub-item 111b has a date options menu including a plurality of return visit dates that are selectable.

For example, the step for creating the follow-up task further includes: in response to an operation of selecting the return visit date sub-item 111b, popping up a date options menu including a plurality of return visit dates; and receiving an operation of selecting a return visit date from the plurality of return visit dates, and displaying the return visit date in the edit box of the return visit date sub-item 111*b*. Then, the creation of the return visit date for the follow-up task may be completed.

In some embodiments, as shown in FIGS. 4A and 4B, the custom area 11 further includes a check box corresponding to each custom item 111. By checking the corresponding check box, a follow-up task corresponding to the target date may be created. For example, considering an example where the date of creating the follow-up task is Jul. 13, 2020, the return-visit dates of the first four custom items 111 are Aug. 14, 2020, Sep. 14, 2020, and Oct. 14, 2020, respectively. If these dates are not the target dates, the corresponding check boxes may not be checked. In the fifth custom item 111, a return visit date may be selected from the plurality of return visit dates, and a check box corresponding to the return visit date may be checked, then a suitable follow-up task may be created.

As a possible design, as shown in FIGS. 4A and 4B, the custom area 11 further includes an add button, and the step for creating the follow-up task further includes: in response to an operation of selecting the add button, displaying a new custom item 111 so as to create a new follow-up task. As for specific steps, reference may be made to the above description, and details will not be repeated here.

In some embodiments, before creating the follow-up task including the follow-up form in S5, the follow-up form management method further includes:

S3, as shown in FIG. 3, in response to an operation instruction for opening a patient management interface, displaying the patient management interface 300. The patient management interface 300 includes basic information of at least one patient and an operation index item 161*a*, and the operation index item 161*a* includes a follow-up index creation item.

In response to the operation instruction for opening the follow-up creation interface, displaying the follow-up creation interface 400 (S4), includes the following steps.

In S41, a tenth operation entered on the patient management interface is received, the tenth operation being used for selecting a follow-up index creation item of a target patient.

For example, as shown in FIG. 3, if the patient X1 is the target patient, the tenth operation is to select the follow-up index creation item 161*a* of the patient X1, so as to create a follow-up for the patient X1.

In S42, in response to the tenth operation, the follow-up creation interface 400 is displayed. The follow-up creation interface 400 further includes a basic information area 12, and the basic information of the target patient is displayed in the basic information area 12.

As shown in FIGS. 4A and 4B, the basic information area 12 displays basic information such as the chronic disease, name, gender, and age of the patient X1.

The solutions provided by the embodiments of the present disclosure are mainly described from the perspective of interaction between various interfaces above. It will be understood that, in order to implement the follow-up form management function, the health management system 1000 provided by the embodiments of the present disclosure includes corresponding hardware structures and/or software modules for executing each function. Those skilled in the art will easily realize that the present disclosure may be implemented in the form of hardware or a combination of hardware and computer software in conjunction with the units and algorithm steps of each example described in the embodiments disclosed herein. Whether a function is executed by hardware or computer software driving hardware depends on the specific application and design constraints of the technical solution. Those skilled may use different methods to implement the described functions for each specific application, but such implementations should not be considered as exceeding the protection scope of the present disclosure.

In the embodiments of the present disclosure, the health management system 1000 may be divided into functional modules according to the above method examples. For example, the health management system may be divided into functional modules corresponding to different functions; or, two or more functions may be integrated into one processing module. The integrated modules may be implemented in the form of hardware, or may be implemented in the form of software functional units. It will be noted that, the division of modules in the embodiments of the present disclosure is schematic, and is only a logical functional division, and there may be other division manners in actual implementation.

In a case where the health management system is divided into functional modules according to different functions, FIG. 13 shows a possible schematic structural diagram of the health management system 1000 involved in the above embodiments. The health management system 1000 includes: a scale making tool module 200A, a follow-up creation module 400A, a patient management module 300A, a follow-up template module 500A, a follow-up management module 600A, and a follow-up task execution module 700A. The scale making tool module 200A is used for supporting the health management system 1000 to perform S2 and the sub-steps included in S2, for example, S21 to S27 in FIG. 9, S21' to S27 in FIG. 10A, S21" to S27 in FIG. 10B, etc. The follow-up creation module 400A is used for supporting the health management system 1000 to perform S5 and the sub-steps included in S5, for example, S51 to S54, and S51' to S54'. The patient management module 300A is used for supporting the health management system 1000 to perform S4 and the sub-steps included in S4, for example, S41 to S42. The follow-up template module 500A is used for supporting the health management system 1000 to perform S9 and the sub-steps included in S9, for example, S91 to S92. The follow-up management module 600A is used for supporting the health management system 1000 to perform S7. The follow-up task execution module 700A is used for supporting the health management system 1000 to perform S8 and the sub-steps included in S8, for example, S81 to S82, and S81' to S82'. Regarding all relevant content of each step involved in the embodiments of the follow-up form management method, reference may be made to the functional description of the corresponding functional module, and details will not be repeated here.

Figure 14:
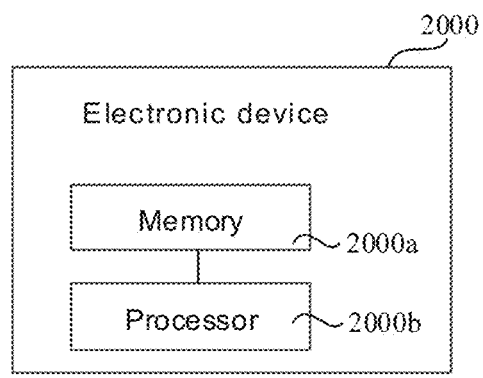
FIG. 14 is a structural diagram of an electronic device, according to some embodiments of the present disclosure.

As shown in FIG. 14, some embodiments of the present disclosure further provide an electronic device 2000, which includes a processor 2000*a* and a memory 2000*b*.

The memory 2000*a* has stored thereon computer program instructions suitable for execution by the processor 2000*b*. When the computer program instructions are run on the processor 2000*b*, the processor 2000*b* performs one or more steps of the follow-up form management method as described in any embodiment of the present disclosure.

The processor 2000*b* may be, for example, a central processing unit (CPU), a general-purpose processor, a digital signal processor (DSP), an application-specific integrated circuit (ASIC), a field programmable gate array (FPGA), or other programmable logic devices, transistor logic devices, hardware components, or any combination thereof. The processor 2000*b* can implement or execute the various exemplary logical blocks, modules and circuits described in the embodiments of the disclosure. The processor may also be a combination that implements computing functions, such as a combination of one or more microprocessors, a combination of a DSP and a microprocessor, etc.

The memory 2000a may be, for example, a random access memory (RAM), a flash memory, a read only memory (ROM), an erasable programmable read only memory (EPROM), an electrically erasable programmable read-only memory (Electrically EPROM, EEPROM), a register, a hard disk, a removable hard disk, a compact disk read only memory (CD-ROM), or any other form of storage medium known in the art. An exemplary storage medium is coupled to the processor, such that the processor can read information from, and write information to, the storage medium. Of course, the storage medium can also be an integral part of the processor.

Some embodiments of the present disclosure further provide a computer-readable storage medium. The computer-readable storage medium has stored thereon computer program instructions that, when run on a processor, cause the processor to perform one or more steps of the follow-up form management method as provided in the embodiments of the present disclosure.

For example, the computer-readable storage medium may include, but are not limited to, a magnetic storage device (e.g., a hard disk, a floppy disk or a magnetic tape), an optical disk (e.g., a compact disk (CD), and a digital versatile disk (DVD)), a smart card and a flash memory device (e.g., an erasable programmable read-only memory (EPROM), a card, a stick or a key driver). Various computer-readable storage media described in the present disclosure may represent one or more devices and/or other machine-readable storage media that are used for storing information. The term "machine-readable storage medium" may include, but is not limited to, wireless channels and various other media capable of storing, containing and/or carrying instructions and/or data.

Some embodiments of the present disclosure further provide a computer program product. The computer program product includes computer program instructions that, when executed on a computer, cause the computer to perform one or more steps of the follow-up form management method as provided in some embodiments of the present disclosure.

Some embodiments of the present disclosure further provide a computer program. When executed on a computer, the computer program causes the computer to perform one or more steps of the follow-up form management method as described in any one of the above embodiments.

Beneficial effects of the computer-readable storage medium, the computer program product, and the computer program are the same as the beneficial effects of the follow-up form management method as described in some of the above embodiments, and details will not be repeated here.

The foregoing descriptions are merely some specific implementation manners of the present disclosure, but the protection scope of the present disclosure is not limited thereto. Any person skilled in the art could conceive of changes of replacements within the technical scope disclosed by the present disclosure, which shall all be included in the protection scope of the present disclosure. Therefore, the protection scope of the present disclosure shall be subject to the protection scope of the claims.

What is claimed is:

1. A follow-up form management method applied to a health management system, comprising:
in response to an operation instruction for opening a scale making tool interface, displaying the scale making tool interface; the scale making tool interface including a field display area and an editing area, the field display area including a plurality of fields, the editing area being used for making a follow-up form, wherein a follow-up form to be made includes a plurality of target elements, and each target element is generated by a field;
in response to an operation instruction for making the follow-up form, making the follow-up form in the editing area;
in response to an operation instruction for opening a follow-up creation interface, displaying the follow-up creation interface, the follow-up creation interface including an options menu, and the options menu including a plurality of options corresponding to the generated follow-up form; and
in response to an operation instruction for creating a follow-up task, creating the follow-up task including a follow-up form, the follow-up form included in the follow-up task being a follow-up form corresponding to an option selected from the options menu under the operation instruction for creating the follow-up task, wherein
in response to the operation instruction for making the follow-up form, making the follow-up form in the editing area, includes:
receiving a first operation entered on the scale making tool interface, the first operation being used for selecting a field from the plurality of fields;
in response to the first operation, displaying the selected field in the editing area; and
receiving and responding to the first operation repeatedly, until fields corresponding to the plurality of target elements required by the follow-up form to be made are all displayed in the editing area, so as to generate the follow-up form;
the plurality of fields include at least one commonly used field, and a commonly used field includes at least one edited property;
the field selected by the first operation is a commonly used field, after displaying the selected field in the editing area, in response to the operation instruction for making the follow-up form, making the follow-up form in the editing area further includes:
in response to the first operation, using the commonly used field displayed in the editing area as the target element; and
the plurality of fields include a plurality of commonly used fields, and the plurality of commonly used fields include at least one common commonly used field and at least one private commonly used field, wherein the common commonly used field is able to be used as a target element in at least two types of follow-up forms to be made, and the private commonly used field is able to be used as a target element in one type of follow-up form to be made.

2. The method according to claim 1, wherein the follow-up creation interface includes a standard template area, and the standard template area includes a template classification selection box; the template classification selection box has a chronic disease options menu, and the chronic disease options menu includes a plurality of chronic disease options; each chronic disease option corresponds to a follow-up template, and each follow-up template includes a plurality of follow-up forms and an interval time corresponding to each follow-up form; and in response to the operation instruction for creating the follow-up task, creating the follow-up task including the follow-up form, includes:
  receiving a second operation entered in the standard template area, the second operation being used for selecting the template classification selection box;
  in response to the second operation, displaying the chronic disease options menu including the plurality of chronic disease options in the standard template area;
  receiving a third operation entered in the standard template area, the third operation being used for selecting a chronic disease option from the plurality of chronic disease options; and
  in response to the third operation, creating a plurality of follow-up tasks in the standard template area; wherein each follow-up task includes a follow-up form and a corresponding return visit time, in each follow-up task, the follow-up form is a follow-up form in a follow-up template corresponding to the selected chronic disease option, and the return visit time is obtained according to a date of creating the follow-up task and the interval time corresponding to the follow-up form.

3. The method according to claim 2, further comprising:
in response to an operation instruction for opening a follow-up template interface, displaying the follow-up template interface; wherein the follow-up template interface includes a template classification bar, and the template classification bar includes the plurality of chronic disease options; and
in response to an operation instruction for creating a follow-up template, creating the follow-up template corresponding to the selected chronic disease option.

4. The method according to claim 3, wherein the follow-up template interface further includes a template content bar; the template content bar includes a new button, and the template content bar is used for displaying the created follow-up template;
  in response to the operation instruction for creating the follow-up template, creating the follow-up template, includes:
    receiving a fourth operation entered in the template classification bar; wherein the fourth operation is used for selecting a chronic disease option from the plurality of chronic disease options and for selecting the new button;
    in response to the fourth operation, displaying a follow-up template creation dialog box on the follow-up template interface; wherein the follow-up template creation dialog box includes a follow-up form edit box and an interval time edit box as well as a confirm button and a cancel button, the follow-up form edit box has at least one form option related to the selected chronic disease option, and each form option corresponding to a generated follow-up form;
    receiving a fifth operation entered in the follow-up form edit box, the fifth operation being used for selecting a form option from the at least one form option;
    in response to the fifth operation, displaying a name of a follow-up form corresponding to the selected form option in the follow-up form edit box;
    receiving a sixth operation entered in the interval time edit box, the sixth operation being used for setting the interval time corresponding to the selected chronic disease option;
    in response to the sixth operation, displaying the set interval time in the interval time edit box;
    receiving a seventh operation entered in the follow-up template creation dialog box, the seventh operation being used for selecting the confirm button; and
    in response to the seventh operation, displaying the follow-up template in the template content bar.

5. The method according to claim 1, wherein the follow-up creation interface includes a custom area; the custom area includes at least one custom item, and each custom item includes a return visit content selection box; the return visit content selection box has a form options menu, the form options menu includes a plurality of form options, and each form option corresponds to a generated follow-up form;
  in response to the operation instruction for creating the follow-up task, creating the follow-up task including the follow-up form, includes:
    receiving an eighth operation entered in the custom area, the eighth operation being used for selecting a return visit content selection box of a custom item;
    in response to the eighth operation, displaying a form options menu, provided in the return visit content selection box of the selected custom item, including a plurality of form options in the custom area;
    receiving a ninth operation entered in the custom area, the ninth operation being used for selecting a form option from the plurality of form options displayed in the custom area; and
    in response to the ninth operation, creating the follow-up task in the custom area, the follow-up task including a follow-up form corresponding to the selected form option.

6. The method according to claim 5, wherein the follow-up task further includes a return visit date;
  the selected custom item by the eighth operation includes a return visit date sub-item;
  the return visit date sub-item has a fixed return visit date; or
  the return visit date sub-item has a date options menu including a plurality of return visit dates that are selectable.

7. The method according to claim 1, further comprising:
before creating the follow-up task including the follow-up form, in response to an operation instruction for opening a patient management interface, displaying the patient management interface; the patient management interface including basic information of at least one patient and an operation index item, and the operation index item including a follow-up index creation item, wherein
in response to the operation instruction for opening the follow-up creation interface, displaying the follow-up creation interface, includes:
  receiving a tenth operation entered on the patient management interface, the tenth operation being used for selecting a follow-up index creation item of a target patient; and
  in response to the tenth operation, displaying the follow-up creation interface; the follow-up creation interface further including a basic information area, and basic information of the target patient being displayed in the basic information area.

8. The method according to claim 1, wherein the plurality of fields include at least one basic field, and each basic field includes at least one property to be edited;
  the field selected by the first operation is a basic field, after displaying the selected field in the editing area, in response to the operation instruction for making the follow-up form, making the follow-up form in the editing area further includes:
  in response to the first operation, displaying a properties menu of the basic field in the editing area, the properties menu including at least one property edit box;
  receiving an eleventh operation entered in the at least one property edit box, the eleventh operation being used for editing a property of the basic field in each property edit box; and
  in response to the eleventh operation, displaying the edited property in each property edit box to generate the target element.

9. The method according to claim 8, wherein the properties menu further includes a save as commonly used field button;
the method further comprises:
  receiving a twelfth operation entered in the properties menu, the twelfth operation being used for selecting the save as commonly used field button; and
  in response to the twelfth operation, displaying the generated target element in the field display area as the commonly used field.

10. The method according to claim 9, wherein the plurality of fields include at least two basic fields, and the at least two basic fields include a first basic field and a second basic field; the first basic field is used for generating a first target element, the second basic field is used for generating a second target element, and a corresponding relationship exists between the first target element and the second target element; at least one property edit box of the first basic field includes a data source property edit box;
  in response to the eleventh operation, displaying the edited property in each property edit box, includes:
    in response to the eleventh operation, displaying a data source property representing the corresponding relationship in the data source property edit box of the first basic field;
  the method further comprises:
  in response to an operation instruction for opening a follow-up task execution interface, displaying the follow-up task execution interface, wherein the follow-up task execution interface includes a follow-up form included in a follow-up task created for a target patient, the follow-up form included in the follow-up task created for the target patient includes the first target element and the second target element, and the first target element and the second target element each have an edit box;
  receiving a thirteenth operation entered in the edit box of the second target element, the thirteenth operation being used for entering target content in the edit box of the second target element;
  in response to the thirteenth operation, displaying the target content in the edit box of the second target element, and automatically displaying content obtained according to the corresponding relationship represented by the data source property in the edit box of the first target element.

11. The method according to claim 9, wherein the plurality of fields include a third basic field; the third basic field is used for generating a third target element, and at least one property edit box of the third basic field includes a data source property edit box;
  in response to the eleventh operation, displaying the edited property in each property edit box, includes:
    in response to the eleventh operation, displaying a data source property linked with a background database in the data source property edit box of the third basic field;
the method further comprises:
  in response to an operation instruction for executing a follow-up task, displaying the follow-up task execution interface; wherein the follow-up task execution interface includes a follow-up form included in a follow-up task created for a target patient, the follow-up form included in the follow-up task created for the target patient includes the third target element, and the third target elements has an edit box;
  receiving a fourteenth operation entered in the edit box of the third target element, the fourteenth operation being used for selecting the edit box of the third target element; and
  in response to the fourteenth operation, automatically displaying content in the background database linked with the data source property of the third target element in the edit box of the third target element.

12. The method according to claim 1, wherein the scale making tool interface further includes a form area and a submission bar; the form area is used for displaying a name of the generated follow-up form, and the submission bar includes a generate form button; and
  in response to the operation instruction for making the follow-up form, making the follow-up form in the editing area further includes:
    receiving a fifteenth operation entered in the submission bar, the fifteenth operation being used for selecting the generate form button, so as to submit and save the generated follow-up form; and
    in response to the fifteenth operation, displaying the name of the saved follow-up form in the form area.

13. The method according to claim 12, wherein the submission bar further includes a preview button; and
  in response to the operation instruction for making the follow-up form, making the follow-up form in the editing area further includes: before receiving the fifteenth operation,
    receiving a sixteenth operation entered in the submission bar, the sixteenth operation being used for selecting the preview button to preview the generated follow-up form; and
    in response to the sixteenth operation, displaying the generated follow-up form in the editing area.

14. The method according to claim 13, wherein the sixteenth operation is further used for selecting a preview effect of the form, the preview effect including a paper effect and an effect displayed on a screen of a mobile terminal;
  in response to the sixteenth operation, displaying the generated follow-up form in the editing area, includes:
    in response to the sixteenth operation, displaying the generated follow-up form in the editing area with the paper effect or with the effect displayed on the screen of the mobile terminal.

15. The method according to claim 12, wherein the form area includes a list sub-area and an operation sub-area; the list sub-area includes a name of at least one saved follow-up form, and a saved form includes a plurality of set elements; the operation sub-area includes at least one import reference option, and each saved form corresponds to an import reference option;
  in response to the operation instruction for making the follow-up form, making the follow-up form in the editing area further includes:

receiving a seventeenth operation entered in the operation sub-area, the seventeenth operation being used for selecting an import reference option of the at least one import reference option;

in response to the seventeenth operation, displaying a saved follow-up form corresponding to the selected import reference option in the editing area; the saved follow-up form corresponding to the selected import reference option being used as a basic form;

receiving an eighteenth operation entered in a form creation interface; the eighteenth operation being used for modifying at least one set element of the plurality of set elements in the basic form, wherein the at least one set element is inconsistent with the plurality of target elements of the follow-up form to be made;

in response to the eighteenth operation, setting the at least one set element that is modified to generate a target element; and receiving and responding to the eighteenth operation repeatedly, until the plurality of set elements of the basic form are consistent with the plurality of target elements of the follow-up form to be made, so as to generate a new follow-up form.

16. An electronic device, comprising: a processor and a memory, wherein
the memory has stored thereon computer program instructions suitable for execution by the processor; when the computer program instructions are run on the processor, the processor performs one or more steps of the follow-up form management method according to claim 1.

17. A non-transitory computer-readable storage medium, wherein the computer-readable storage medium has stored thereon computer program instructions that, when run on a processor, cause the processor to perform one or more steps of the follow-up form management method according to claim 1.

* * * * *